United States Patent
Durgin et al.

[11] Patent Number: 6,030,364
[45] Date of Patent: Feb. 29, 2000

[54] APPARATUS AND METHOD FOR PERCUTANEOUS PLACEMENT OF GASTRO-INTESTINAL TUBES

[75] Inventors: Russ Durgin, Attleboro; Sheila Caira, Auburndale, both of Mass.

[73] Assignee: Boston Scientific Corporation, Natick, Mass.

[21] Appl. No.: 08/943,829

[22] Filed: Oct. 3, 1997

[51] Int. Cl.[7] .................................................. A61M 5/178
[52] U.S. Cl. ........................... 604/164; 604/158; 604/27; 604/171; 604/264
[58] Field of Search ............................. 604/158, 27, 160, 604/161, 164, 166, 171, 264, 198; 606/191

[56] References Cited

U.S. PATENT DOCUMENTS

| | | |
|---|---|---|
| 3,253,594 | 5/1966 | Matthews et al. . |
| 3,530,860 | 9/1970 | Majoros . |
| 3,786,810 | 1/1974 | Pannier et al. . |
| 4,077,412 | 3/1978 | Moossun . |
| 4,112,932 | 9/1978 | Chiulli . |
| 4,412,832 | 11/1983 | Kling et al. . |
| 4,738,666 | 4/1988 | Fuqua . |
| 4,862,891 | 9/1989 | Smith . |
| 4,921,479 | 5/1990 | Grayzel et al. . |
| 4,983,168 | 1/1991 | Moorehead . |
| 5,015,239 | 5/1991 | Browne . |
| 5,074,846 | 12/1991 | Clegg et al. . |
| 5,112,308 | 5/1992 | Olsen et al. . |
| 5,139,486 | 8/1992 | Moss . |
| 5,151,086 | 9/1992 | Duh et al. . |
| 5,158,545 | 10/1992 | Trudell et al. . |
| 5,167,627 | 12/1992 | Clegg et al. . |
| 5,176,649 | 1/1993 | Wakabayashi . |
| 5,183,464 | 2/1993 | Dubrul et al. . |
| 5,209,736 | 5/1993 | Stephens et al. . |
| 5,246,424 | 9/1993 | Wilk . |
| 5,263,937 | 11/1993 | Shipp . |
| 5,275,583 | 1/1994 | Crainich . |
| 5,275,611 | 1/1994 | Behl . |
| 5,312,360 | 5/1994 | Behl . |
| 5,344,420 | 9/1994 | Hilal et al. . |
| 5,346,459 | 9/1994 | Allen . |
| 5,364,372 | 11/1994 | Danks et al. . |
| 5,431,676 | 7/1995 | Dubrul et al. . |
| 5,437,644 | 8/1995 | Nobles . |
| 5,443,484 | 8/1995 | Kirsch et al. . |
| 5,454,790 | 10/1995 | Dubrul ..................................... 604/104 |
| 5,531,678 | 7/1996 | Tomba et al. . |
| 5,533,977 | 7/1996 | Netcalf et al. . |
| 5,536,255 | 7/1996 | Moss . |
| 5,545,141 | 8/1996 | Eld . |
| 5,573,517 | 11/1996 | Bonutti et al. . |
| 5,577,993 | 11/1996 | Zhu et al. . |
| 5,584,847 | 12/1996 | Duluco et al. . |
| 5,824,002 | 10/1998 | Gentelia et al. ........................ 604/164 |

FOREIGN PATENT DOCUMENTS

WO 97/20399   11/1992   WIPO .

*Primary Examiner*—Corrine McDermott
*Assistant Examiner*—Kent Gring
*Attorney, Agent, or Firm*—Kenyon & Kenyon

[57] ABSTRACT

A method and apparatus for the percutaneous placement of gastro-intestinal tubes, the apparatus comprising a longitudinal penetration device; a hollow, tapered dilator; and a sheath having a central lumen extending therethrough. The penetration device is placed within the sheath, pushed distally to penetrate the target organ, and then removed from the sheath. After the penetration device is removed, the dilator is inserted into the central lumen of the sheath until it penetrates the target organ, so that the sheath and the penetration are radially dilated as the dilator passes through the sheath. The sheath is then pulled in the proximal direction to counter-balance the distal insertion force. A gastro-intestinal tube is inserted into the hollow center, and pushed distally until it exits the distal end of the dilator. The dilator and sheath are then removed from the target organ.

41 Claims, 19 Drawing Sheets

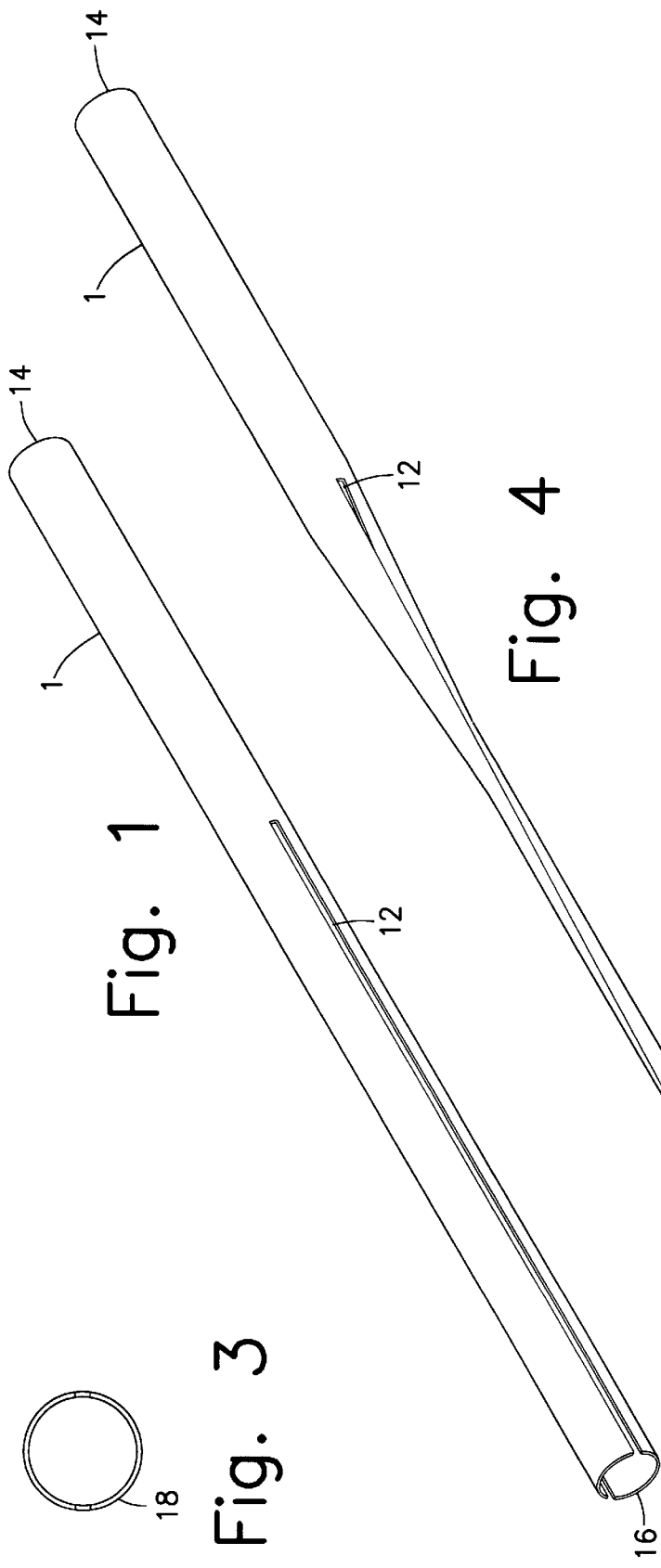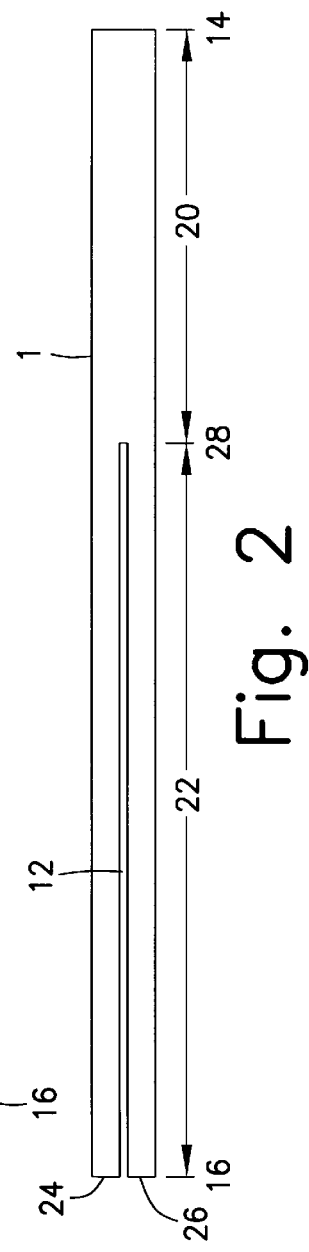

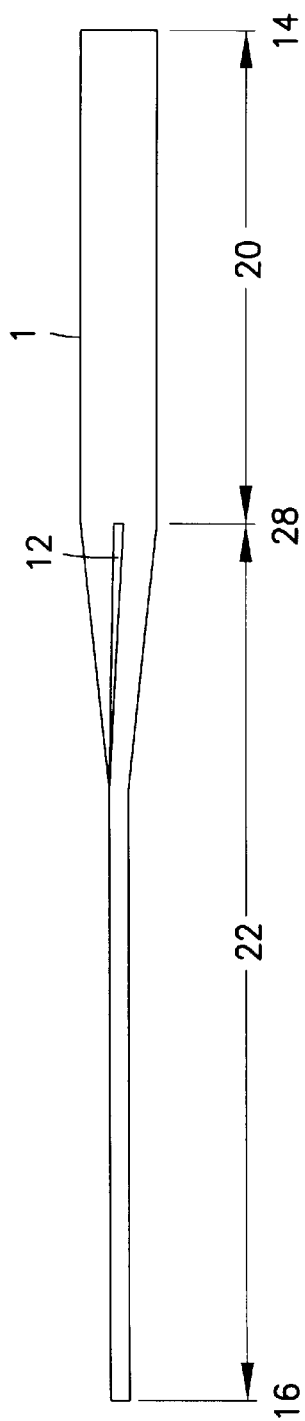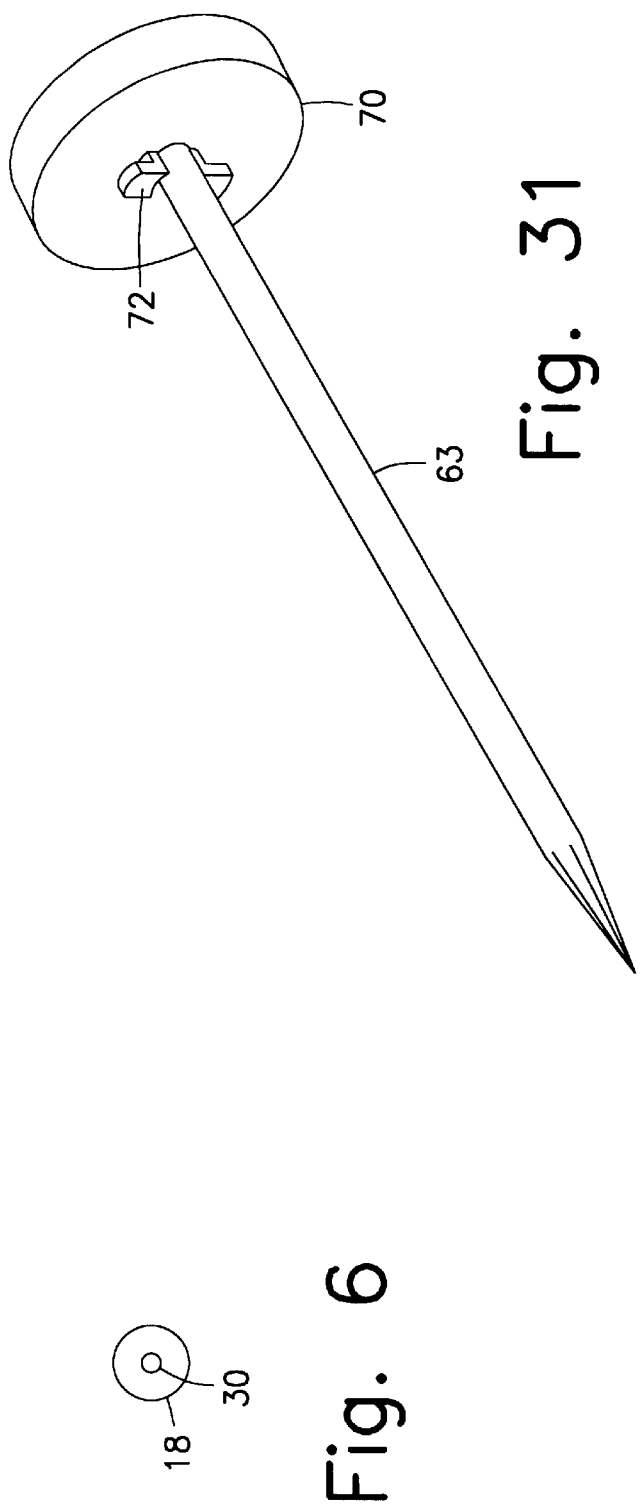

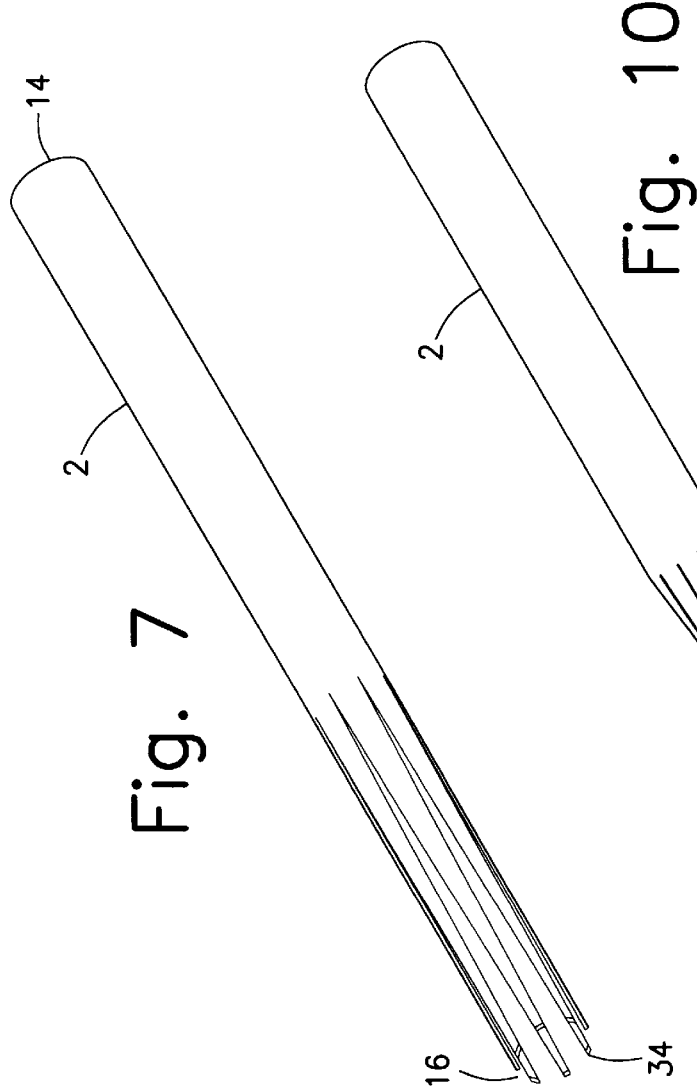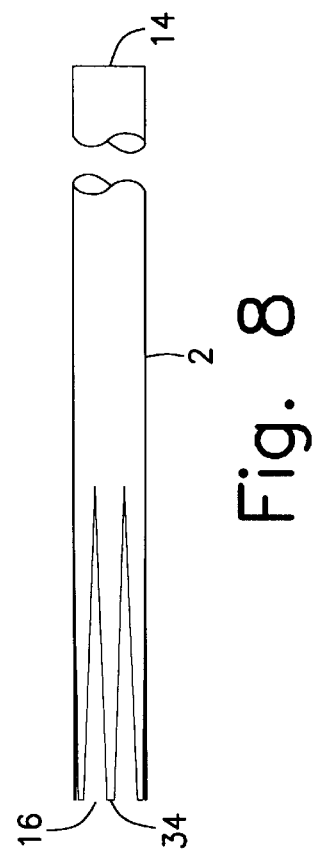

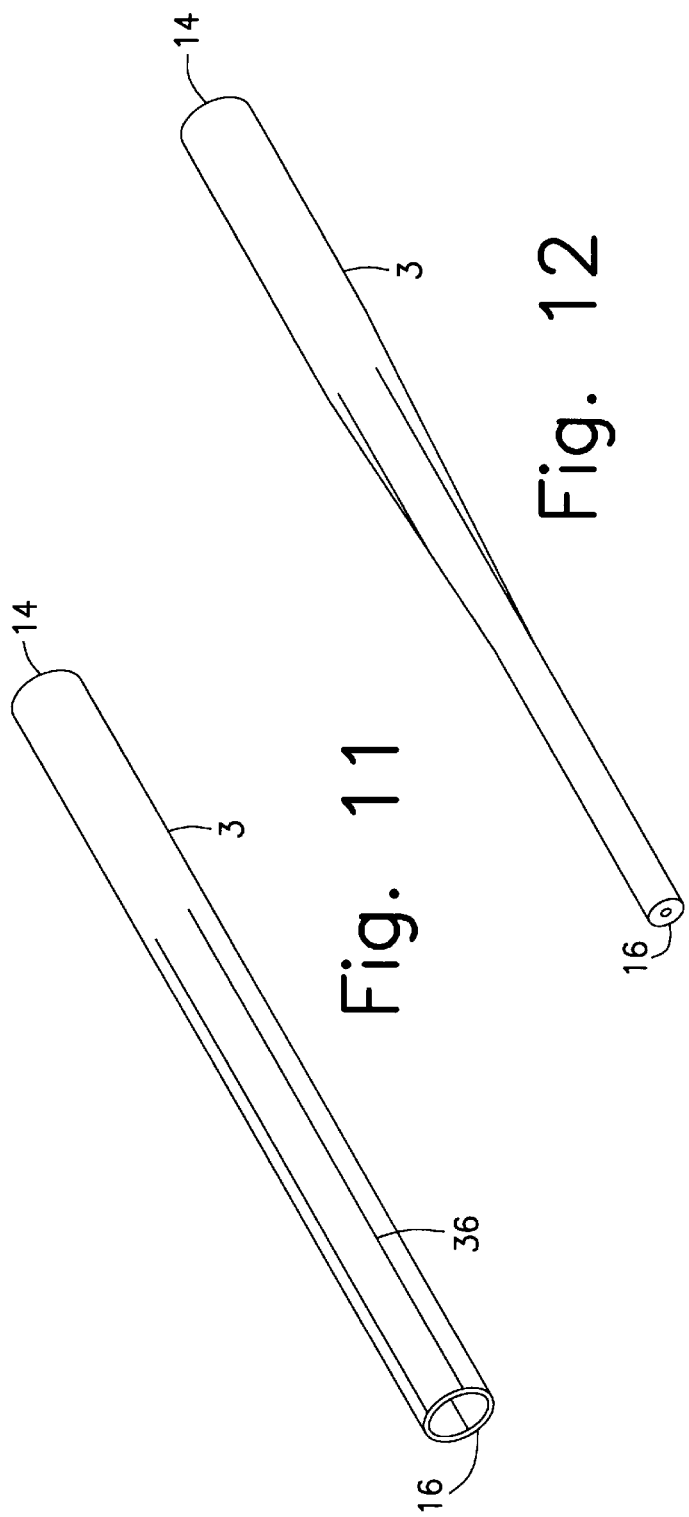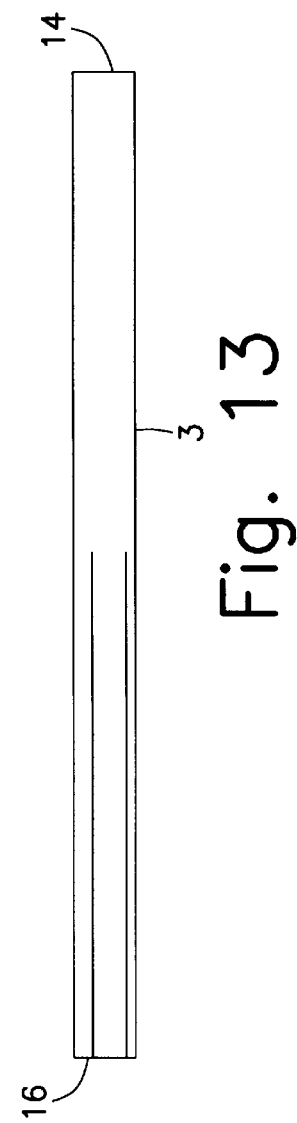

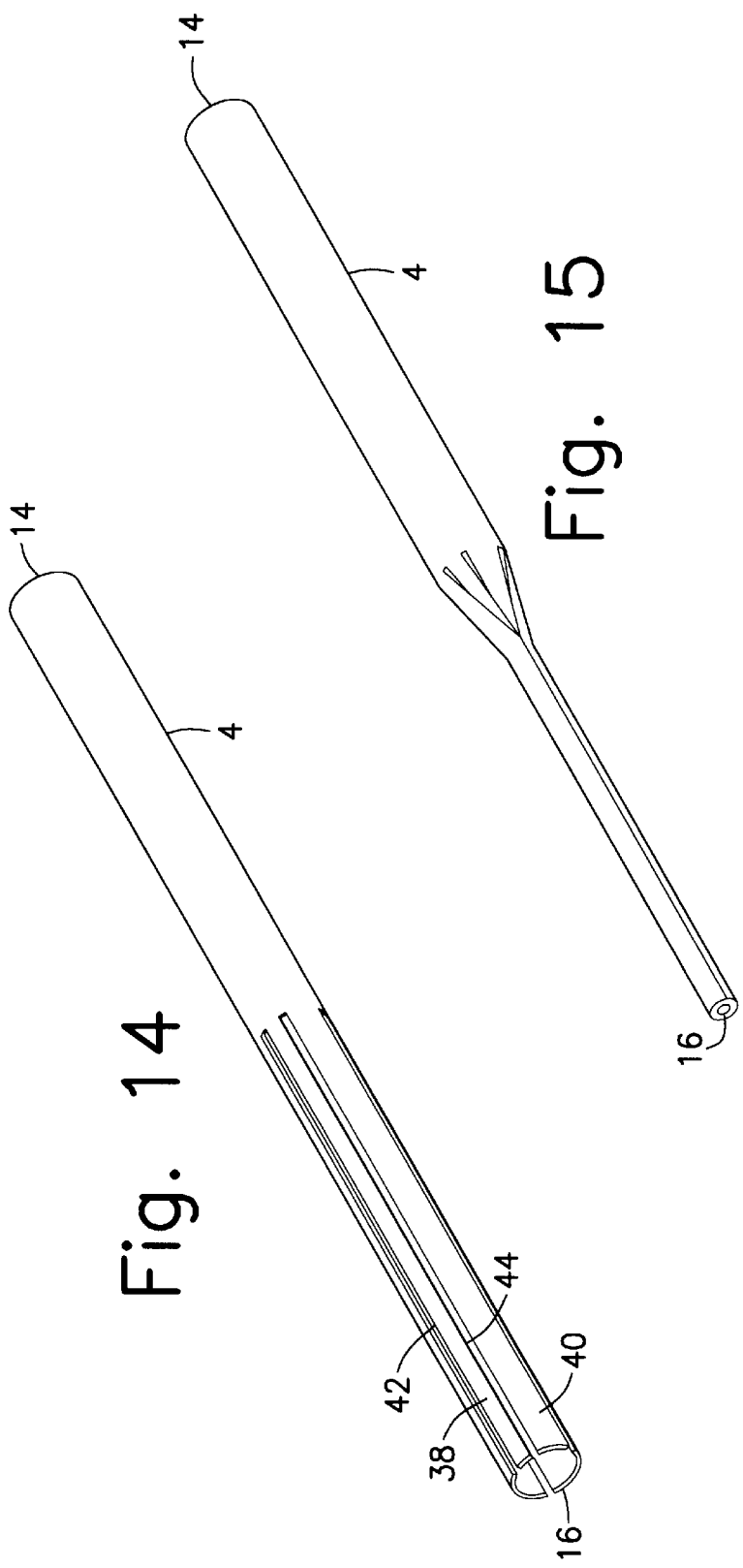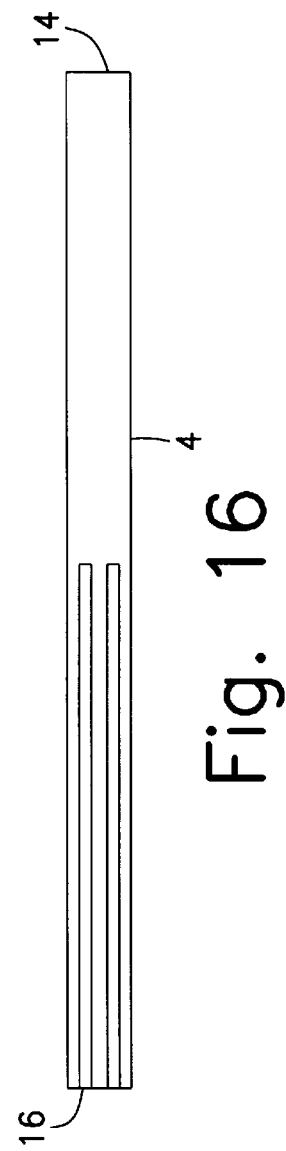

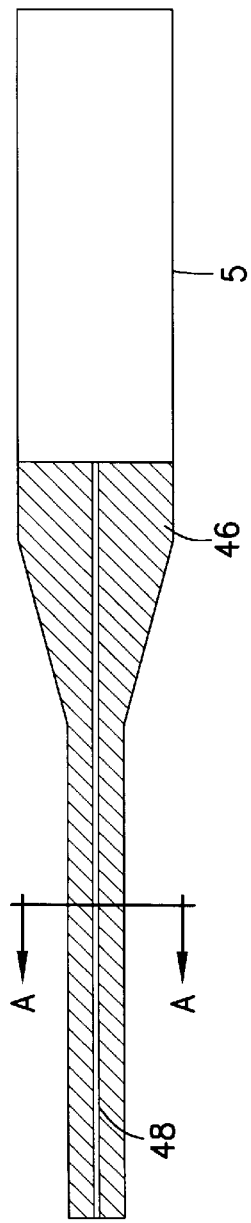
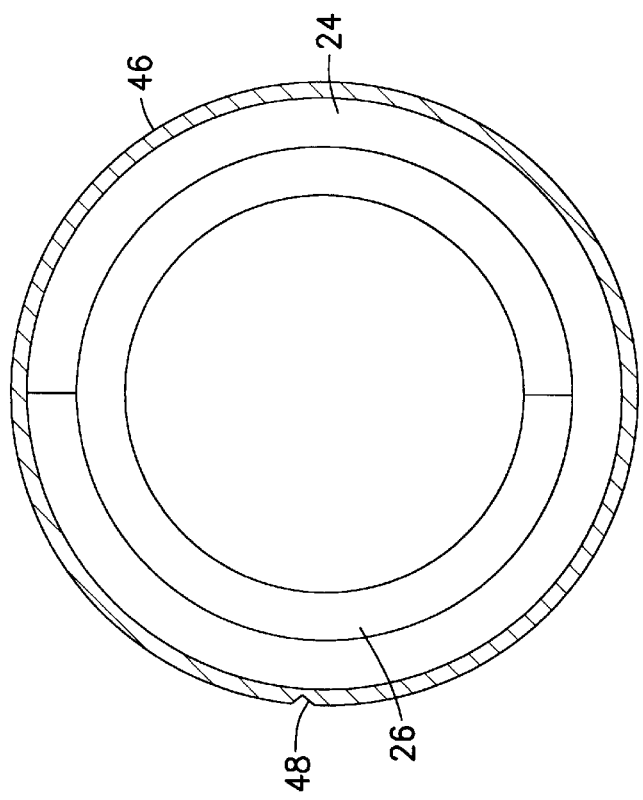
Fig. 17
Fig. 18

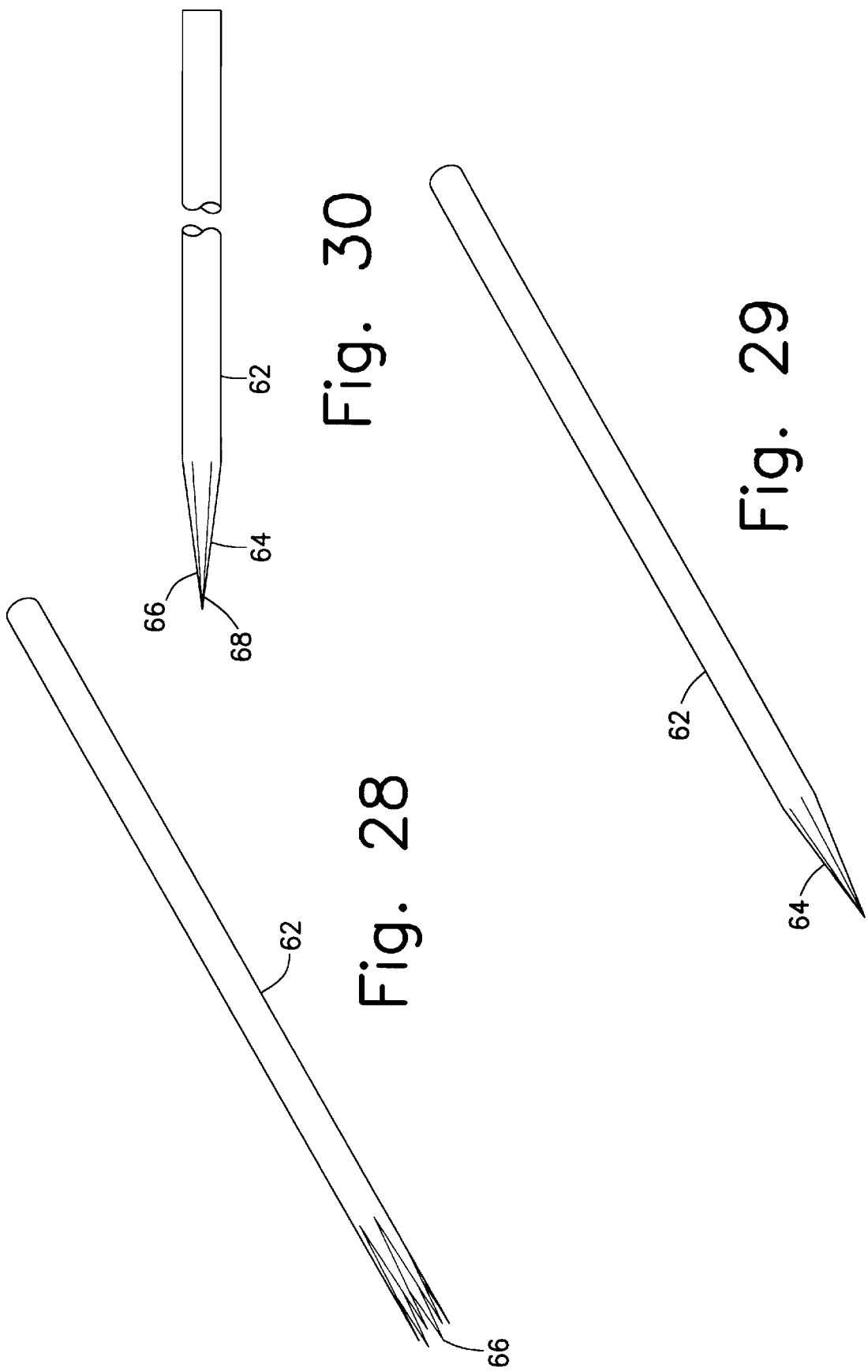

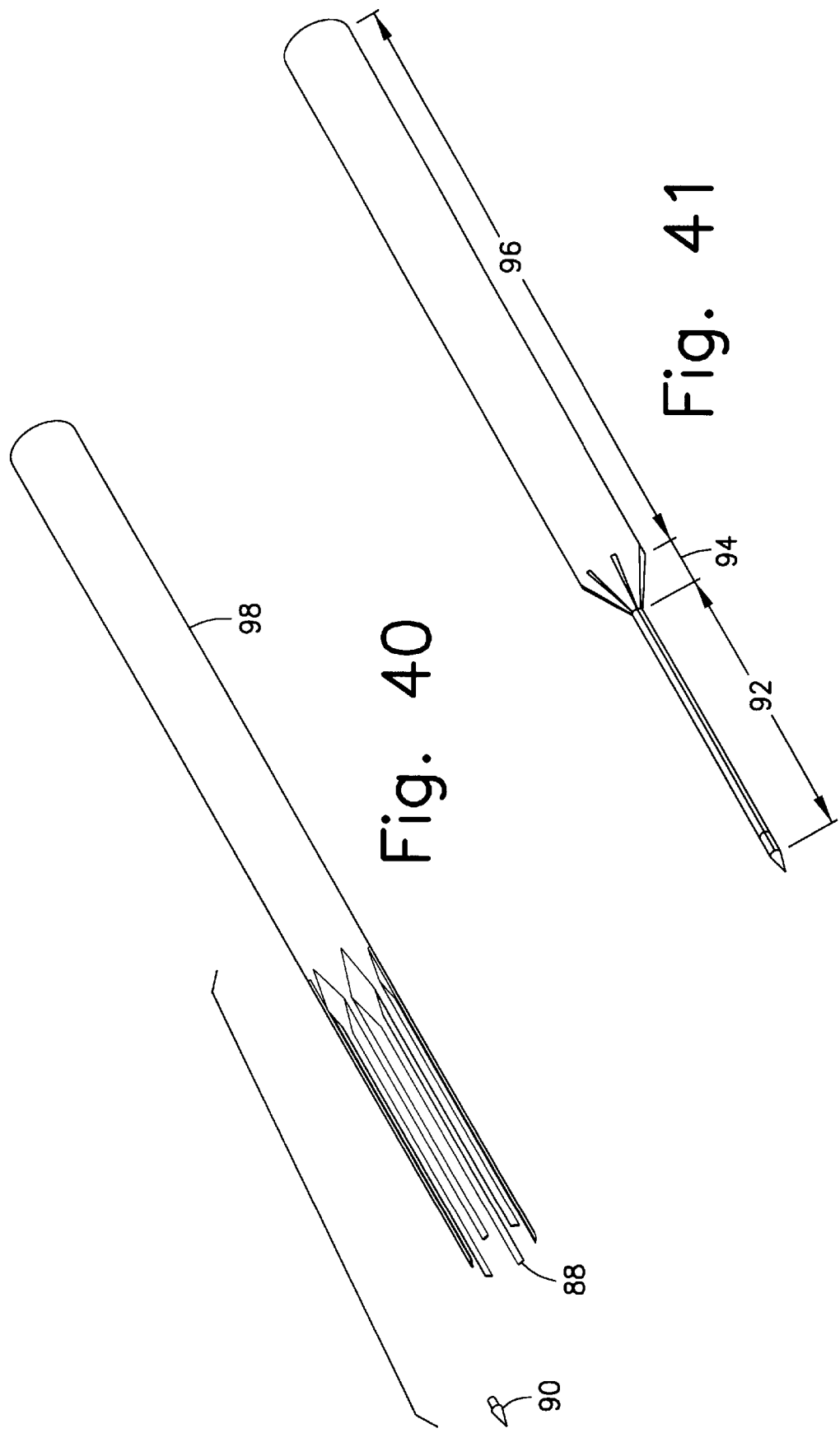

APPARATUS AND METHOD FOR PERCUTANEOUS PLACEMENT OF GASTRO-INTESTINAL TUBES

FIELD OF THE INVENTION

The present invention relates generally to an apparatus and method for the percutaneous placement of gastro-intestinal tubes. More specifically, the present invention relates to an apparatus and method for percutaneously placing gastro-intestinal tubes by creating a percutaneous penetration, then enlarging the penetration using counter-balanced dilation.

BACKGROUND OF THE INVENTION

Numerous procedures exist for inserting medical devices into a patient's body percutaneously, i.e. through the skin. Various abdominal surgical procedures utilize laparoscopic techniques which allow the percutaneous penetration of surgical tools without making a large skin incision. Other techniques utilize percutaneous endoscopic gastrostomy (PEG) to place gastrostomy tubes.

Laparoscopic techniques for establishing a surgical port typically involve inserting an insufflating needle within a sheath and pushing the needle/sheath assembly through the skin and into the abdomen. The needle is used to inflate the abdominal cavity with an insufflating gas. Once the abdomen is insufflated, the needle is removed from inside the sheath and a trocar is inserted into the central lumen of a fixed diameter access port. The trocar and the access port are then inserted into the initial penetration site, through the sheath, and forced into the abdomen. The trocar and the sheath are then removed, leaving the access port in place for use during surgery.

The trocars used in laparoscopy usually have a knife-like tapered distal end with two sharp leading edges extending from the main trocar body to the distal end. The sharp leading edges form a wedge which is as wide as the trocar diameter at the point of attachment to the main body and tapers distally ending in a sharp distal tip. This large cutting edge slices through tissue during insertion, causing trauma to the body tissue and increasing healing time. Additionally, when using such trocars, surgeons risk damaging the target organ or other organs if they fail to stop the distal insertion force of the trocar in a timely fashion or if they fail to properly control the forces associated with such penetration. Some laparoscopic trocars have been equipped with distally-biased sheaths which automatically cover the leading edge upon penetration of the target organ wall (e.g., U.S. Pat. No. 5,346,459, the contents of which are incorporated herein by reference.) Other trocars have an electrically charged tip for cutting tissue. Once the tip has penetrated the target organ, the electrical supply is cut off. (See U.S. Pat. No. 5,344,420.) Although these improved trocars prevent damaging organs subsequent to target organ penetration, they do little to lessen the trauma to abdominal tissue during penetration.

Three main percutaneous endoscopic gastrostomy techniques are used to place gastrostomy tubes within the stomach: Sacks-Vine, Ponsky, and Russell.

The Sacks-Vine technique involves inserting an endoscope into the patient's mouth, down the esophagus, and into the stomach; insufflating the stomach, and then using endoscopic illumination to locate the optimal percutaneous penetration point. A special needle, having a penetrating portion and a surrounding cannula, is then inserted through the abdominal wall and into the stomach so that it penetrates at the located point. The needle is removed, leaving the cannula in place, and a guidewire is inserted through the cannula. An endoscope snare is then used to grab the guidewire from inside the stomach and pull it up the esophagus and out the mouth. Next, a gastrostomy tube, with a tapered catheter attached to its distal end, is inserted over the guidewire down into the stomach. The guidewire is then used to pull the catheter through the percutaneous penetration. Finally, the catheter is then cut from the gastrostomy tube, leaving the tube in place within the stomach.

With the Ponsky technique, a wire with a looped end is attached to a needle, inserted through the abdominal wall and into the stomach. An endoscope snare is used to hook the loop and pull the wire up the esophagus and out the mouth. A second wire with fixed loop is attached to the distal end of a tapered catheter. The proximal end of the catheter is then attached to the distal end of a gastrostomy tube. Next, the loop of the percutaneously inserted wire is then hooked to the wire attached to the tapered catheter. The percutaneously inserted wire is then pulled from outside the abdominal wall, drawing the tube down the esophagus, into the stomach, and out the insertion site. The catheter is then cut from the gastrostomy tube, leaving the tube in place within the stomach.

With the Russell technique, a needle is percutaneously inserted into the stomach, and a guidewire is inserted into the stomach through the needle. The needle is removed, leaving the guidewire in place, and a series of tapered dilators with increasingly larger diameters are inserted one at a time over the guidewire and into the stomach. Each dilator insertion increases the size of the penetration. The final dilator may have a removable sheath which is inserted into the stomach along with the dilator. The final dilator is then removed, leaving the sheath in place. The gastrostomy tube can then be inserted through the sheath and into the stomach. The sheath is then removed from around the tube.

Practitioners have encountered numerous problems when using these prior art PEG techniques. The Sacks-Vine is a complicated and cumbersome technique which often requires more than one person to perform. In addition, dragging the gastrostomy tube through the esophagus often leads to extreme patient discomfort, trauma to esophagus, internal bleeding, and sometimes gastro-esophageal reflux condition. Furthermore, both the Sacks-Vine and Ponsky techniques entail dragging tube and wire through mouth, esophagus, stomach, and abdominal wall which increases the risk of abdominal infection.

In the Russell procedure, the dilator must closely follow the line of the guidewire, so as not to buckle the wire into the peritoneal cavity. If the wire were to buckle, the practitioner might force the dilator into contact with the stomach at a site other than the optimal penetration site, damaging the stomach or other organs. This need to prevent wire buckling during insertion slows down the placement procedure.

In addition, the Russell technique involves forcibly inserting a dilator into the stomach wall through a penetration smaller than the dilator diameter. The stomach wall is quite thick and will indent, or tent, when pushed distally by the dilator. Any attempt to dilate a tented stomach wall by continuing the distal force increases the risk of damaging the stomach or surrounding organs. To aid in dilation when using the Russell technique, practitioners often employ a twisting motion during insertion. This twisting motion increases trauma to tissues of the abdominal and stomach walls.

The tendency of the stomach wall to tent during dilation makes percutaneous placement of gastrostomy tubes difficult. In a tented state, the anterior stomach wall is pushed closer to the posterior stomach wall. Tenting increases the risk that the practitioner will pierce both the anterior and posterior walls during dilation.

Tenting can lead to improper placement of the tube as well. The medical practitioner performing the procedure must be careful to fully penetrate the stomach wall during dilation. If the tube placement is attempted without complete dilator penetration, the practitioner may inadvertently place the tube within the peritoneal cavity, instead of the target organ. Such improper placement can have fatal consequences. The peritoneal cavity, located between the peritoneum and the stomach, is sterile and susceptible to infection. Because peritoneal infection often goes undetected until it has become severe and internal bleeding occurs, improper tube placement can have fatal consequences.

Numerous devices for radially expanding a penetration can be found in the prior art. Examples of the various prior art devices are found in U.S. Pat. Nos. 5,183,464, 5,431,676, 5,573,517, the contents of which are hereby incorporated by reference.

Additional examples of apparatus and methods for percutaneously placing access tubes can be found in U.S. Pat. Nos. 5,454,790, 5,577,993, and 5,312,360, the contents of which are also hereby incorporated by reference.

There is a need for an apparatus which prevents the target organ wall (e.g. the wall of the stomach) from tenting during percutaneous placement of gastro-intestinal tubes. There is also a need for an apparatus that does not prolong patient recovery by causing tissue trauma during such placement, and a method for percutaneously placing gastrostomy tubes which prevents organ tenting, minimizes tissue trauma.

SUMMARY OF THE INVENTION

The present invention provides both an apparatus and a method for percutaneous placement of gastrostomy tubes which overcome the deficiencies in the prior art.

The apparatus of the present invention includes a radially expandable sheath, an insertion device, and a hollow dilator. The radially expandable sheath has proximal and distal ends, a major diameter section, and a minor diameter section. The major diameter section, which is preferably a solid tube, is located towards the proximal end of the sheath and has a major diameter. The minor diameter section is that portion of the sheath that extends from the distal end of the major diameter section to the distal end of the sheath, and has a minor diameter at its distal end.

The minor diameter section is comprised of longitudinal fingers which can be formed by splitting the sheath longitudinally or removing longitudinal pieces from the sheath body. The fingers are then folded or overlapped such that the diameter of the sheath at the distal end is smaller than the diameter at the distal end of the major diameter section. This folding or overlapping may be effected via elastic forces within the sheath that so urge the fingers together.

The apparatus of the present invention also includes a penetration device, which is a rod-like structure with a piercing means at its distal end. It will be known to those skilled in the art that the penetration device may be a trocar, a needle, or the like. The piercing means may be solid or tubular. The device is inserted through the sheath so that the piercing means is distal to the distal end of the sheath. To facilitate insertion, the distal end of the penetration device has an outer diameter which allows it to pass through the inner diameter of the sheath's distal end. The piercing means may be tapered to allow easier removal from the sheath.

The apparatus of the present invention also includes a hollow dilator. The hollow dilator is a hollow, rigid or semi-rigid, thin-walled tube with a tapered distal end. The tapered distal end is comprised of fingers formed by splitting the dilator longitudinally, removing longitudinal pieces from the dilator body, or a combination thereof. Preferably, the fingers are formed by removing triangular pieces from the dilator body, and thereby creating pointed fingers.

The tapered distal end is formed by folding or overlapping the fingers and drawing them to a point. The tapered end may be formed such that the fingers are normally drawn to a point. In such a formation, the fingers can be opened once the dilator reaches the target site by applying a distal force to the fingers from inside the dilator.

Alternatively, the fingers can be formed such that they are normally open or untapered. The fingers are forced closed prior to insertion, and held closed as the dilator passes through the sheath, by the sheath and surrounding tissue. The fingers resume the normally opened position once the dilator penetrated the inner cavity of the target organ. This embodiment facilitates gastrostomy tube insertion by reducing the force necessary to place the tube after dilation.

According to the method of the present invention, the target organ is insufflated and a percutaneous penetration site is located endoscopically. An assembly of the sheath and penetration device assembly is then inserted into the patient's body under direct scope visualization. (Preferably, both the loading of the penetration device within the sheath and the sheath formation take place at the factory, and the resulting device is shipped as a pre-loaded assembly.) The pre-loaded assembly is then inserted into the patient's body. Alternatively, at the time the procedure is being performed, the radially expandable sheath is tapered and assembled such that the piercing means of an penetration device is distal of the sheath's distal end. The piercing means of the penetration device punctures the skin, and the assembly is advanced through the skin, fat layer, fascia and peritoneum of the abdominal wall. The assembly is further advanced through wall of the target organ until the sheath is observed within the organ cavity. The penetration device is then withdrawn from inside the sheath, while leaving the sheath in place.

In a preferred embodiment, the sheath has a means for maintaining insufflation pressure after the penetration device is removed. In one embodiment, the sheath has a hub with a valve comprised of a thin, flat elastomeric disk with a pilot hole for receiving the penetration device and dilator. This valve can maintain a constant seal by expanding around the penetration device and dilator as they are inserted, and retracting as they are removed. In another embodiment, the sheath has a coating or covering which extends past the distal end of the sheath to cover a portion of the penetration device, and has a very narrow opening at the distal end. The narrow opening in the extending portion creates a valve which prevents premature release of the insufflation gas from target organ. Valves of this type are well known in the art.

The sheath provides a narrow penetration which extends from the outside of the abdomen to the inside of the target organ cavity.

The gastrostomy tube to be placed is pre-loaded, that is, inserted into the dilator prior to dilator insertion. The tapered distal end of the dilator is then inserted into the proximal end of the sheath's major diameter, and advanced distally. Simultaneously, the sheath is pulled proximally so as to counter-balance the distal force from the dilator insertion.

The medical practitioner can perform the dilation by pushing distally on the dilator with one hand, while simultaneously pulling proximally on the sheath with the other. Although this counter-balancing of forces maintains the approximate sheath position within the target organ throughout dilator insertion, additional tolerance for sheath displacement may be desired. This can be accomplished by penetrating the target organ cavity with the sheath for an additional distance.

The method of the present invention provides for safer, faster, and easier placement of gastro-intestinal tubes. Without the counter-balancing proximal force, the distal dilator insertion force would be opposed only by the natural resistance of the target organ itself and the insufflation pressure, which can be as low as 15 mm Hg. If pushed distally by the large diameter dilator the organ wall would be displaced distally from its planar position, at the point of attempted insertion. This change in planar position is called "tenting." Tenting makes organ wall penetration difficult and increases the risk of post-operative infection.

The placement method of the present invention reduces organ tenting. Counter-balancing the distal insertion force by proximally pulling the sheath with approximately the same force reduces the degree to which the target organ wall is pushed from its planar position.

As the dilator passes through the minor diameter section of the sheath, the sheath fingers and surrounding tissue are radially displaced. The counter-balancing causes the distally-directed insertion force, which is applied in the plane perpendicular to the organ wall, to be transferred radially, or to the plane parallel to the organ wall. The natural elasticity of the body tissue allows the narrow initial penetration to be expanded to a size capable of receiving a gastrostomy tube.

When the dilator is in position, an extension rod is placed into its proximal end. The rod is pushed distally against the pre-loaded gastrostomy tube, while the sheath and dilator are held in position. When the dilator fingers are formed such that they are normally closed, the distal force of the tube and extension rod force the dilator fingers to expand radially, or open out. When the fingers are formed such that they are normally open, the fingers open upon penetration of the target organ. The rod is pushed distally until the tube exits the dilator.

The rod, sheath, and dilator are then removed from the anatomy. The sheath and dilator can be removed first, as the rod position is maintained. Maintaining the rod position prevents the tube from slipping out of the target organ. The rod can then be removed, leaving the tube in place. Alternatively, the rod, sheath, and dilator can be removed at the same time. After those devices have been removed, the tube can then be adjusted, the proximal end can be trimmed, and the tube can be secured.

The present method does not require the complicated procedures of trans-oral placement. The method of the present invention is also preferable to prior art techniques because it prevents tenting of the target organ wall during dilation. The present method also provides a fast and easy way to place non-elastic tubes such as operative ports for instrument or scope access.

BRIEF DESCRIPTION OF THE DRAWINGS

The invention will be more readily understood through the following detailed description, with reference to the accompanying drawings, in which:

FIG. 1 is a perspective view of a first embodiment of a sheath constructed according to the principles of the present invention before the distal fingers are folded.

FIG. 2 is a side view of a two-slit sheath, shown in FIG. 1, again before the distal fingers are folded.

FIG. 3 is an end view of the two-slit sheath, shown in FIGS. 1 and 2.

FIG. 4 is a perspective view of a two-slit sheath according to the present invention in, which the distal fingers are folded.

FIG. 5 illustrates a side view of the two-slit sheath shown in FIG. 4, again with the distal fingers folded.

FIG. 6 is an end view of the two-slit sheath shown in FIGS. 4 and 5.

FIG. 7 is a perspective view of a second embodiment of a sheath constructed according to the principles of the invention, as seen before its distal fingers are folded.

FIG. 8 is a side view of the sheath shown in FIG. 7, again before the distal fingers are folded.

FIG. 9 is an end view of the sheath shown in FIGS. 7 and 8.

FIG. 10 is a perspective view of the second embodiment of a sheath constructed according to the principles of the invention, in which the distal fingers are folded.

FIG. 11 is a perspective view of a third embodiment of a sheath constructed according to the principles of the invention of the present invention before the distal fingers are folded.

FIG. 12 is a perspective view of the third embodiment of a sheath of the present invention in which the distal fingers are folded.

FIG. 13 is a side view of a third embodiment of a sheath shown in FIG. 11, again before the distal fingers are folded.

FIG. 14 is a perspective view of a fourth embodiment of a sheath constructed according to the principles of the present invention before the distal fingers are folded.

FIG. 15 is a perspective view of a fourth embodiment of a sheath constructed according to the principles of the invention in which the distal fingers have been folded.

FIG. 16 is a side view of a fourth embodiment of the sheath shown in FIG. 14.

FIG. 17 is a side view of of a sheath constructed according to the principles of the present invention, in which the sheath has a longitudinally-scored covering.

FIG. 18 is a cross-sectional view of a sheath shown in FIG. 17, taken along section A-A shown in FIG. 17.

FIG. 28 is a perspective view of a first embodiment of a hollow dilator constructed according to the principles of the invention, before the fingers are folded.

FIG. 29 is a perspective view of the first embodiment of the hollow dilator constructed according to the principles of the invention in which the fingers have been folded.

FIG. 30 is a longitudinally cross-sectional view of a first embodiment of a hollow dilator shown in FIG. 29, again with fingers folded.

FIG. 31 is a perspective view of a dilator constructed according to the principles of the present invention with a hub attached to its proximal end.

FIG. 40 is a perspective view of a second embodiment of a hollow dilator constructed according to the principles of the invention, before the fingers have been folded, and with a piercing means shown unattached.

FIG. 41 is a perspective view of the second embodiment of a hollow dilator shown in FIG. 40.

DETAILED DESCRIPTION OF THE INVENTION

Figure 22:
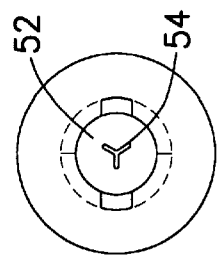
FIG. 22 is a proximal end view of a sheath hub constructed according to the principles of the invention, in which the hub has a valve with multiple slits.

The preferred embodiment of the apparatus of the present invention comprises a radially expandable sheath 1 (shown in FIG. 4), a penetration device 58 (shown in FIG. 26), and a hollow dilator 62 (shown in FIG. 30). Those elements are described in detail below.

Although various embodiments of these elements are described in detail below, in general, they cooperate in a like manner. The penetration device 58 is placed within the sheath 1, pushed distally to penetrate the target organ, and then removed from the sheath 1. After the penetration device 58 is removed, the dilator 62 is inserted into the central lumen of the sheath 1 until it penetrates the target organ, so that the sheath 1 and the penetration are radially dilated as the dilator 62 passes through the sheath 1. The sheath 1 is pulled in the proximal direction to counter-balance the distal insertion force. A gastro-intestinal tube is inserted into the hollow center of the dilator 62, and pushed distally until it exits the distal end of the dilator 62. The dilator 62 and sheath 1 are then removed from the target organ.

FIGS. 1–3 show a first embodiment of a radially expandable generally tubular sheath in which the sheath is shown in the unfolded state. The radially expandable sheath 1 has a proximal end 14, a distal end 16, a major diameter section 20, and a minor diameter section 22. The-major diameter section 20 is located towards the proximal end 14 of the sheath 1 and has a diameter, called the major diameter. The sheath is preferably thin-walled and made of a flexible or semi-rigid material, such as a thermoplastic elastomer, thermoset, fabric, or a combination thereof.

The minor diameter section 22 of the sheath 1 is that portion extending from the distal end of the major diameter section 28 to the distal end of the sheath 16 and is comprised of split fingers 24 and 26. In the embodiments of the sheath shown in FIGS. 1 and 2 the sheath fingers 24 and 26 are formed by removing two longitudinal slices 12 from the sheath body 1. The length of the minor diameter section can vary, but does not normally exceed the thickness of the anatomy which must be percutaneously pierced to place the gastrostomy tube. Most patients have an abdominal wall which is between 2 and 10 cm thick. Accordingly, the length of the minor diameter section should normally lie within that range. The length can be increased, however, to provide for greater sheath displacement tolerance.

FIG. 3 shows the radially expandable sheath 1 in its unfolded state, as viewed from its distal end 16. In this embodiment, the unfolded sheath 1 has a diameter equal to the major diameter along its entire length. However, the sheath 1 may be formed such that, in the unfolded state, the diameter of the minor diameter section 22 decreases distally along the sheath 1 and has a diameter at the distal end 16, called the minor diameter, which is smaller than the major diameter.

FIGS. 4–6 show the sheath 1 of the first embodiment in the folded state. The fingers 24 and 26 are folded or overlapped such that the sheath diameter decreases from the distal end of the major diameter section 28 to the distal end of the sheath 16. FIG. 4 shows a preferred embodiment of a two-slit sheath. The minor diameter section has a consistent diameter (i.e. the minor diameter) for most of its length, with a small proximal portion being tapered to transition from the major diameter to the minor diameter. Alternatively, a larger portion of the minor diameter section's length can consist of the tapered transition portion.

FIG. 6 shows the sheath 1 in the folded state, as viewed from the distal end 16. In the folded state, the distal end of the minor diameter section 22 has a minor diameter 30 which is less than the major diameter 18 of the major diameter section 20. The minor diameter 30 is of a size capable of surrounding the penetration device 58 and penetrating the anatomy with the insertion device 58. The minor diameter section 22 is preferably formed such that the outer diameter at its distal end 30 does not exceed 5 mm. The major diameter portion 20 has a major diameter 18 which will normally be in the 7 to 20 mm. range, but can be larger.

FIGS. 7–9 show an alternative embodiment of a radially expandable sheath 2 in which the fingers 34 are formed by removing longitudinal slices such that the finger width decreases distally. Forming the fingers 34 in this manner facilitates the tapering process by decreasing the amount of finger overlap upon folding. The folding can be achieved by simply folding the fingers 34 such that the finger edges touch, as shown in FIG. 10. In this embodiment, the tapered transition portion may be a larger part of the minor diameter section 22 than in the previously described embodiment.

FIGS. 11–13 show a third embodiment of a radially expandable sheath 3, in which the fingers 36 are formed by slitting the minor diameter section 22 longitudinally. The fingers 36 are then folded and overlapped, as shown in FIG. 12.

The number of fingers 36 present, and the manner in which the minor diameter section 22 is formed may be dependent on the size of the gastrostomy tube to be placed. The larger the tube, the larger the major diameter must be to accommodate the tube. As the major diameter increases, so does the amount of material which can be used to form fingers 36. If no longitudinal portions are removed when forming fingers for sheaths with large major diameters, finger overlap may cause the sheath diameter at the distal end to become too large for easy insertion. Thus, when forming sheaths with larger major diameters, longitudinal portions may be removed to decrease the amount of material overlap during folding. These portions can be removed such that overlap is reduced, while coverage during dilator insertion is maximized. The fingers 36 need not completely cover the anatomy as the dilator 62 is inserted, however. As the dilator 62 passes through the sheath 10, the penetration in the surrounding tissue will expand even without complete circumferential coverage.

FIGS. 14–16 show a fourth embodiment of a radially expandable sheath 4, in which the fingers 38 are formed of variable widths which allows them to be successively wrapped, such that the longitudinal edges of each finger (e.g. 42 and 44) touch on each successive wrap. FIG. 14 shows a sheath 4 with fingers formed with different widths (e.g. 38 and 40). When folding the fingers according to the present embodiment, the smallest finger 38 is wrapped such that the finger's longitudinal edges 42 and 44 touch. Next, a finger with a larger width 40 is wrapped around the previous finger 38 such that its longitudinal edges touch. The remainder of the fingers are similarly wrapped, as shown in FIG. 15.

Besides the method of forming the fingers and minor diameter section, the sheath embodiments described above are essentially same. The same materials can used to construct sheaths according to either of the embodiments. The sheath 1 is thin-walled and made of a flexible or semi-rigid material, such as a thermoplastic (e.g. nylon, polyethylene, PVC, or polyester), a thermoplastic elastomer, thermoset, fabric, or a combination thereof. The major diameter 20 of the sheath 1 is preferably a solid tube, which can either be formed as a continuous extrusion, or can be die cut from a flat sheet, folded such that the longitudinal edges overlap, and bonded along the area of overlap.

The outside surface of the sheath 1 may be treated to increase the friction between the sheath 1 and the surrounding tissue upon insertion. Such treatment could include producing a pimpled or other rough outer surface, or undercutting the surface to produce a grooved surface. This treated surface assists in maintaining the sheath position during dilator insertion. The sheath 5 may additionally have a thin rigid coating 46 over the fingers 24 and 26 which maintains the shape of the minor diameter section during percutaneous placement, as shown in FIGS. 17 and 18. The rigid coating 46 can split or, tear away during dilator placement. The coating 46 may be longitudinally scored to facilitate the splitting or tearing. FIGS. 17 and 18 show a coating 46 with a longitudinal score 48.

Alternatively, the sheath 1 may have an elastomeric coating which maintains the sheath's shape during percutaneous placement. Such a coating either tears away or expands during dilation. Examples of elastomeric coatings include thermoplastic elastomers, thermoplastic rubbers, urethanes, latex, and silicone.

Figure 21:
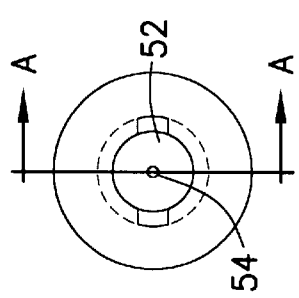
FIG. 21 is a proximal end view of a sheath hub constructed according to the principles of the invention, in which the hub has a valve with a pilot hole.
Figure 23:
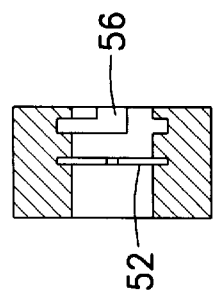
FIG. 23 is a longitudinally cross-sectional view of a sheath hub constructed according to the principles of the invention.
Figure 19:
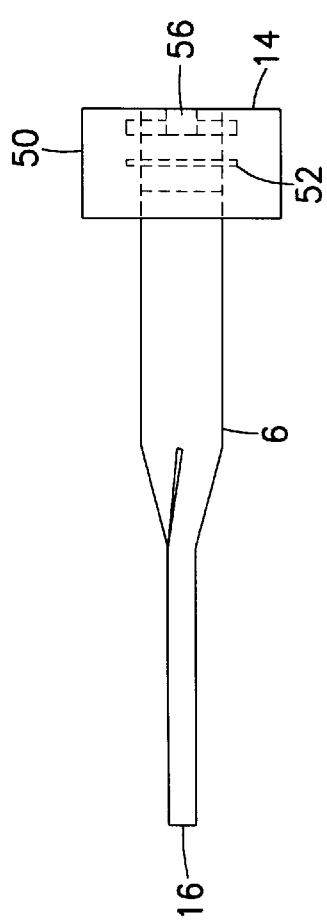
FIG. 19 is a side view of a sheath consructed according to the principles of the invention, partially in section, with a hub located at its proximal end.
Figure 20:
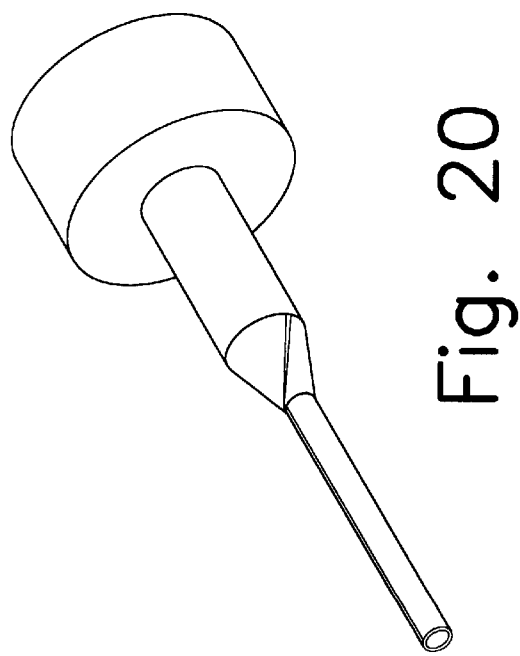
FIG. 20 is a perspective view of the sheath shown in FIG. 19, again with a hub located at its proximal end.

FIGS. 19 and 20 show a sheath 6 with a hub portion 50 on the proximal end 14 which provides a handle for the clinician to hold during sheath insertion and dilation. The hub portion 50 may contain an insufflation gas valve 52 which prevents the gas from escaping from the target organ prematurely, as shown in FIGS. 21 through 23. The valve 52 is comprised of a thin, flat elastomeric disk with a small opening 54. FIG. 21 shows a valve opening which is essentially a pilot hole. FIG. 22 shows an opening formed by making two slits in the elastomeric disk. The opening in the valve material expands to accommodate the penetration device 58, but contracts to prevent insufflation gas from escaping once the penetration device 58 is removed. Similarly, the opening 54 expands to accommodate the dilator 62 during dilator insertion, but contracts upon dilator removal. The valve is preferably made of an elastomer such as silicone or latex, a thermoplastic elastomer, or a thermoplastic rubber.

Figure 25:
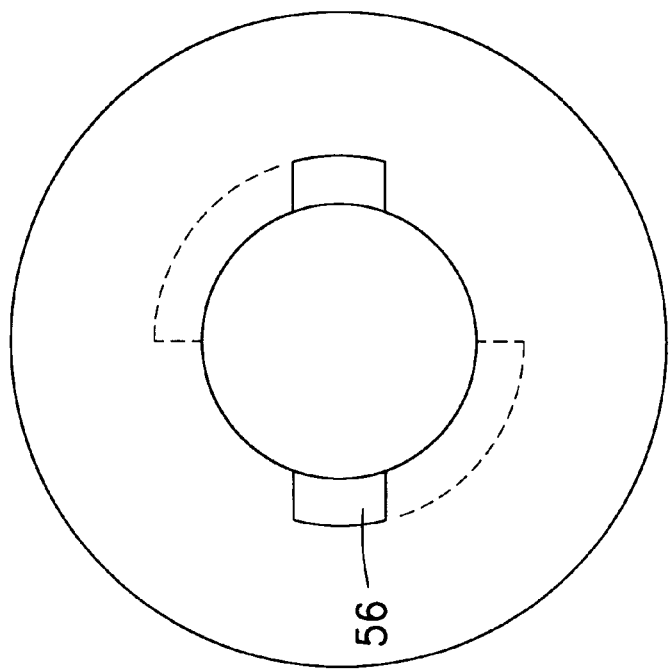
FIG. 25 is an end view of the hub locking mechanism shown in FIG. 24.
Figure 24:
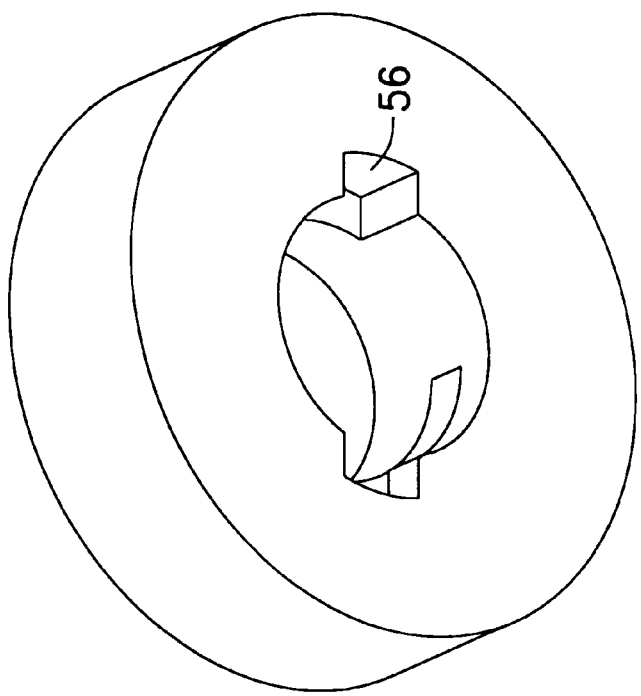
FIG. 24 is a perspective view of a hub locking mechanism constructed according to the principles of the invention.

The hub portion 50 may also have a locking mechanism 56 which mates with a dilator locking mechanism 72 of a dilator hub 70 to secure the dilator 62. FIGS. 24 and 25 show an example of a such a sheath locking mechanism 56. FIG. 31 shows a mating dilator locking mechanism 72. In addition, the hub portion 50 can be used to provide an attachment site for a mechanical dilation device.

Figure 26:
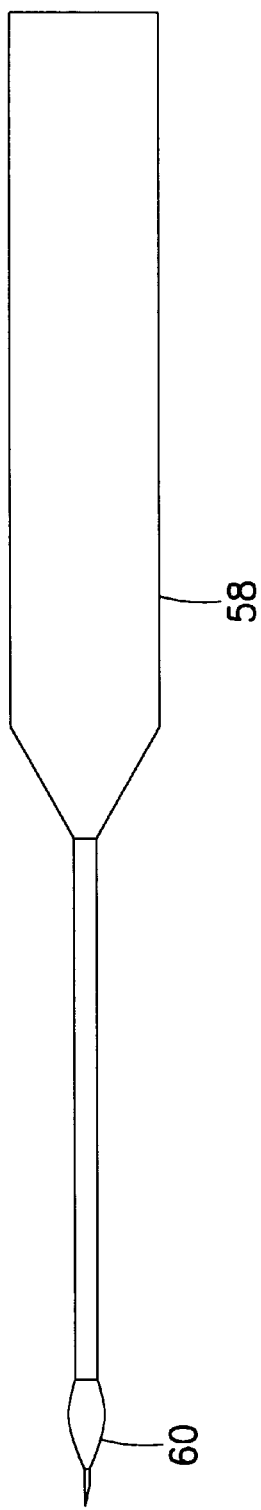
FIG. 26 is a side view of a penetration device constructed according to the principles of the invention.

FIG. 26 shows an penetration device 58 according to the present invention. The penetration device 58 is rod-like device with a piercing means 60 at its distal end which is capable of penetrating human tissue. It will be known to those skilled in the art that the penetration device 58 may be alternatively be a trocar, a needle, or the like. The piercing means 60 may be solid or tubular.

Figure 27:
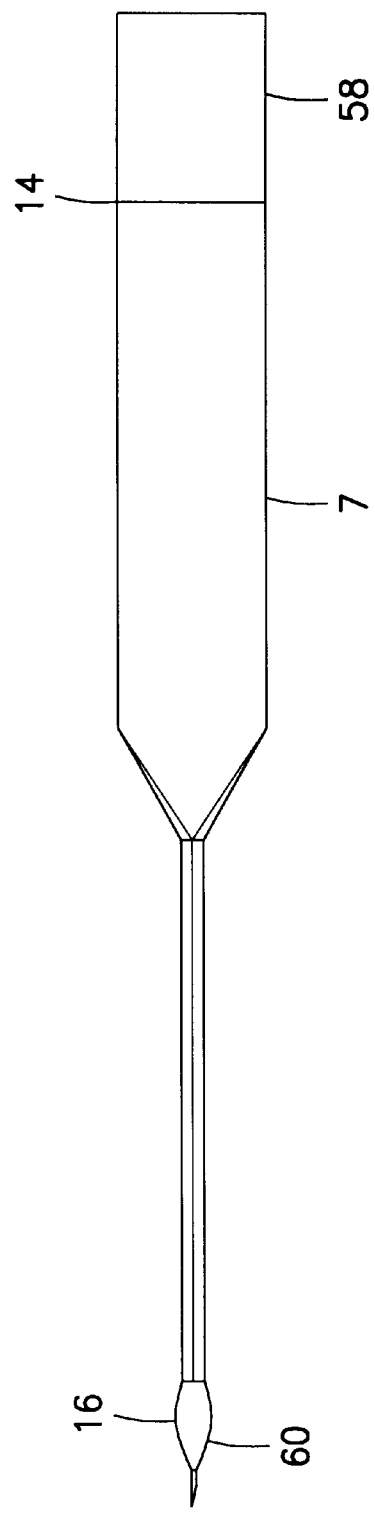
FIG. 27 is a side view of a sheath with an penetration device placed within the central lumen thereof constructed according to the principles of the invention.
Figure 32:
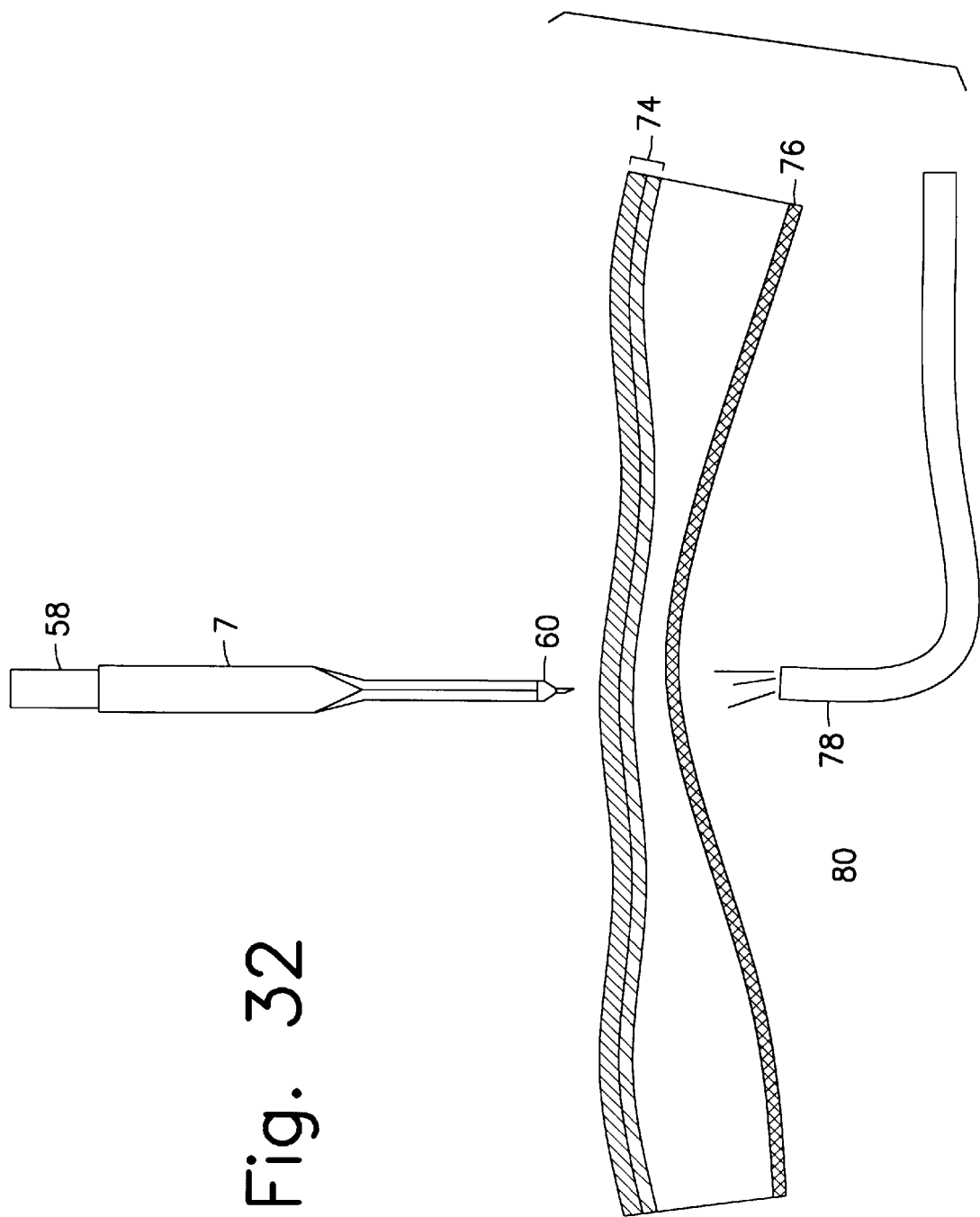
FIGS. 32–38 illustrate the percutaneous placement method of the present invention.

The device 58 is inserted through the sheath 10 so that the piercing means 60 is distal to the distal end 16 of the sheath 7, as shown in FIG. 27. To facilitate insertion, the distal end of the penetration device 60 has an outer diameter which allows it to pass through the inner diameter of the distal end of said sheath 7. In addition, the piercing means 60 may be tapered, as shown in FIG. 26, to allow easy insertion into and removal from the sheath 7. The distal taper of the piercing means facilitates insertion. The proximal taper provides a tapered edge adjacent to which the distal end of the sheath 7 can sit, as shown in FIG. 32. This tapered configuration decreases the likelihood that the distal end of the sheath 7 will catch on the body tissue during insertion, as it allows the distal end of the sheath 7 to rest in a position of lesser radial diameter with respect to the diameter of the piercing means 60 which is just distal to the proximal taper. The proximal taper also prevent the penetration device 58 from catching the sheath 7 during removal of the penetration device 58.

The sheath fingers (e.g. 24 and 26) may be folded before the penetration device 58 is placed within the sheath 10. Alternatively, the sheath fingers can be folded or wrapped around the penetration device 58 after the device 58 is first placed within sheath 7 after its fingers have been folded. In addition, the sheath 7 and penetration device 58 can be shipped to the clinicians as a pre-loaded assembly; or the sheath 7 can be shipped unassembled, and and assembled prior to or at the time of tube placement.

The apparatus of the present invention also includes a hollow dilator 62 which is insertable within the radially expandable sheath 10. The hollow dilator 62 is a hollow, rigid or semi-rigid, thin-walled tube with a tapered distal end 64. FIGS. 28 and 29 show a first embodiment of the hollow dilator 62. In the preferred embodiment, the tapered distal end 64 is formed by first removing longitudinal sections of the tubular body such that fingers 66 are formed whose widths decrease distally, as shown in FIG. 28. Tapering is performed by then drawing the fingers 66 to a point, as shown in FIG. 29. Alternatively, the tapered distal end 64 could be formed by first slitting the distal end of the tubular body longitudinally to form the fingers, then folding or overlapping the fingers and drawing them to a point. The distal end 64, however, need not be a perfect point. It must only be sufficiently tapered to allow insertion.

The tapered end may be formed such that the fingers 66 are normally drawn to a point. In such a formation, the fingers 66 can be opened once the dilator 62 reaches the target site, by applying a distal force to the fingers 66 from inside the dilator 62. Alternatively, the fingers 66 can be formed such that they are normally open or untapered. In this configuration, the fingers 66 are closed prior to insertion into the sheath 10. The force applied on the tapered end during dilator insertion keep the dilator 62 in the tapered position as the dilator 62 passes through the radially expandable sheath 10. The fingers 66 can also be formed such that they are forced closed by the sheath 10 and the body tissue as they resist the dilator insertion force. The fingers 66 of the normally open dilator expand out once the dilator 62 penetrates the inner cavity of the target organ. This embodiment facilitates gastrostomy tube insertion by eliminating the need to force the dilator fingers open during tube insertion, and thus reducing the force necessary to place the tube.

The tapered distal end 64 may be formed such that it is conical in shape, as shown in FIG. 29, but may also have other geometries. For example, when viewing the dilator cross-section longitudinally, as in FIG. 30, the edges 66 and 68 of the tapered distal end 64 can appear elliptical, parabolic, as radii, or as a combination of geometries.

The proximal end may have a hub 70 which facilitates insertion and removal of the dilator 63, as shown in FIG. 31. The hub 70 may also have a locking mechanism 72 which mates with a sheath 56. The mating mechanisms 72 and 56 hold the dilator within the sheath after dilation, thus facilitating tube placement. Numerous locking mechanisms are known in the art.

The dilator 62 is preferably made of a thermoplastic, but can also be made of metal, thermoset or a composite.

Referring now to FIGS. 32–38, the method of percutaneously placement a gastrostomy tube using the present invention will be described in detail.

Methods of using an endoscope to locate an insertion site on the gastric mucosa are well known in the art of percutaneous endoscopic gastrostomy (PEG). In the known methods, the gastric cavity is first insufflated. An endoscope 78 is used to illuminate the abdomen from inside the gastric cavity 80 and locate a site for percutaneous penetration, as shown in FIG. 32.

Figure 33:
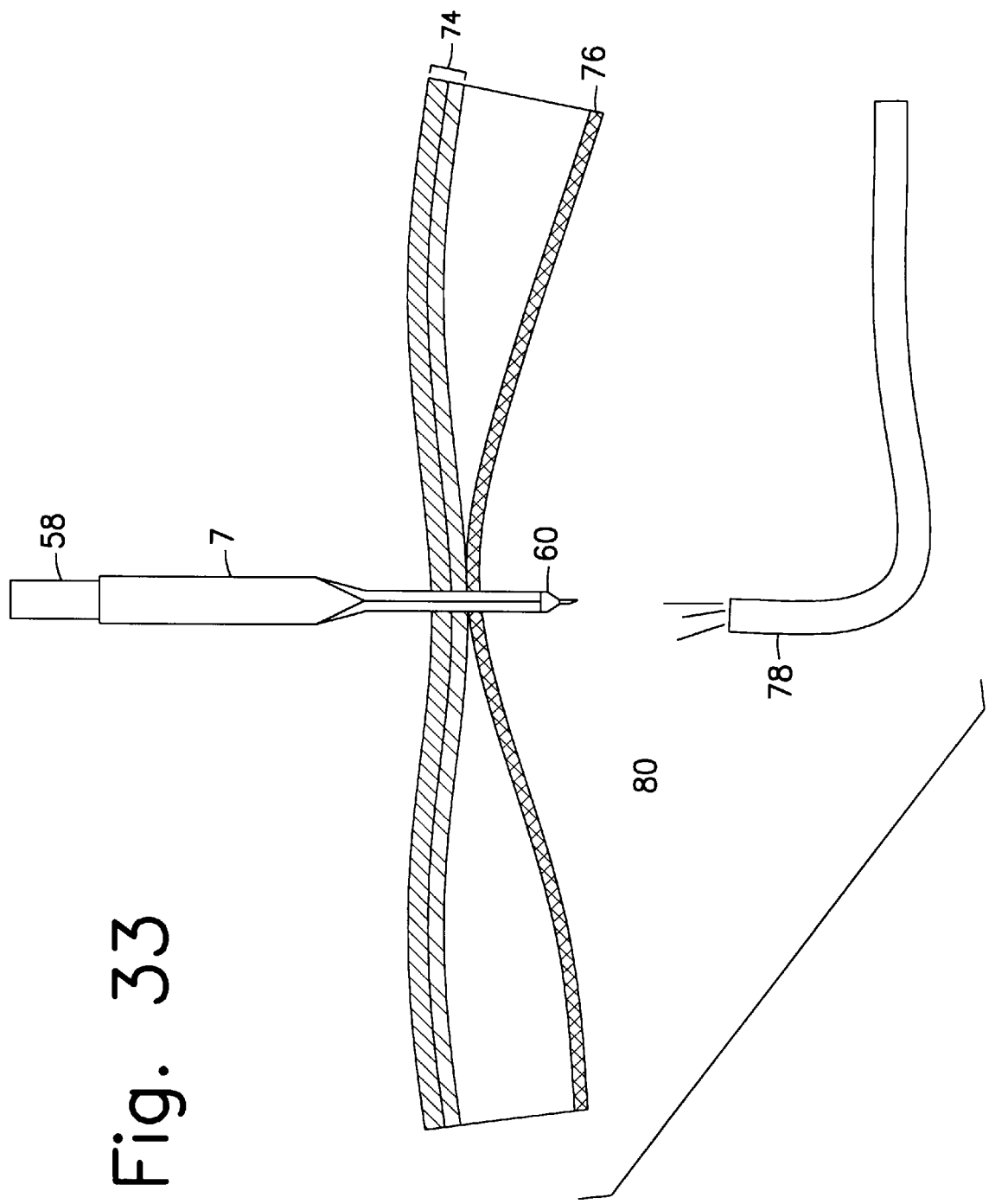
Figure 34:
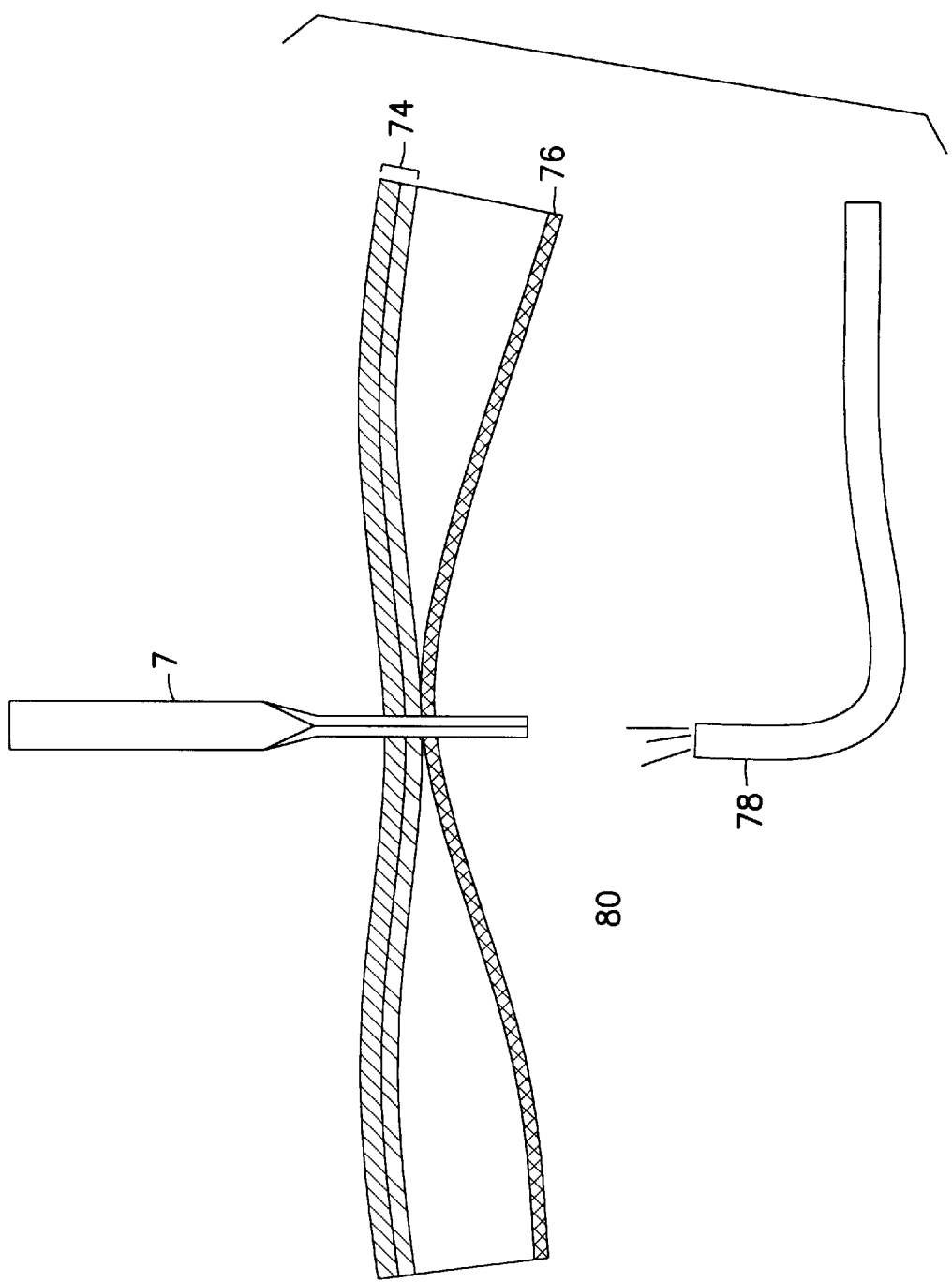
Figure 35:
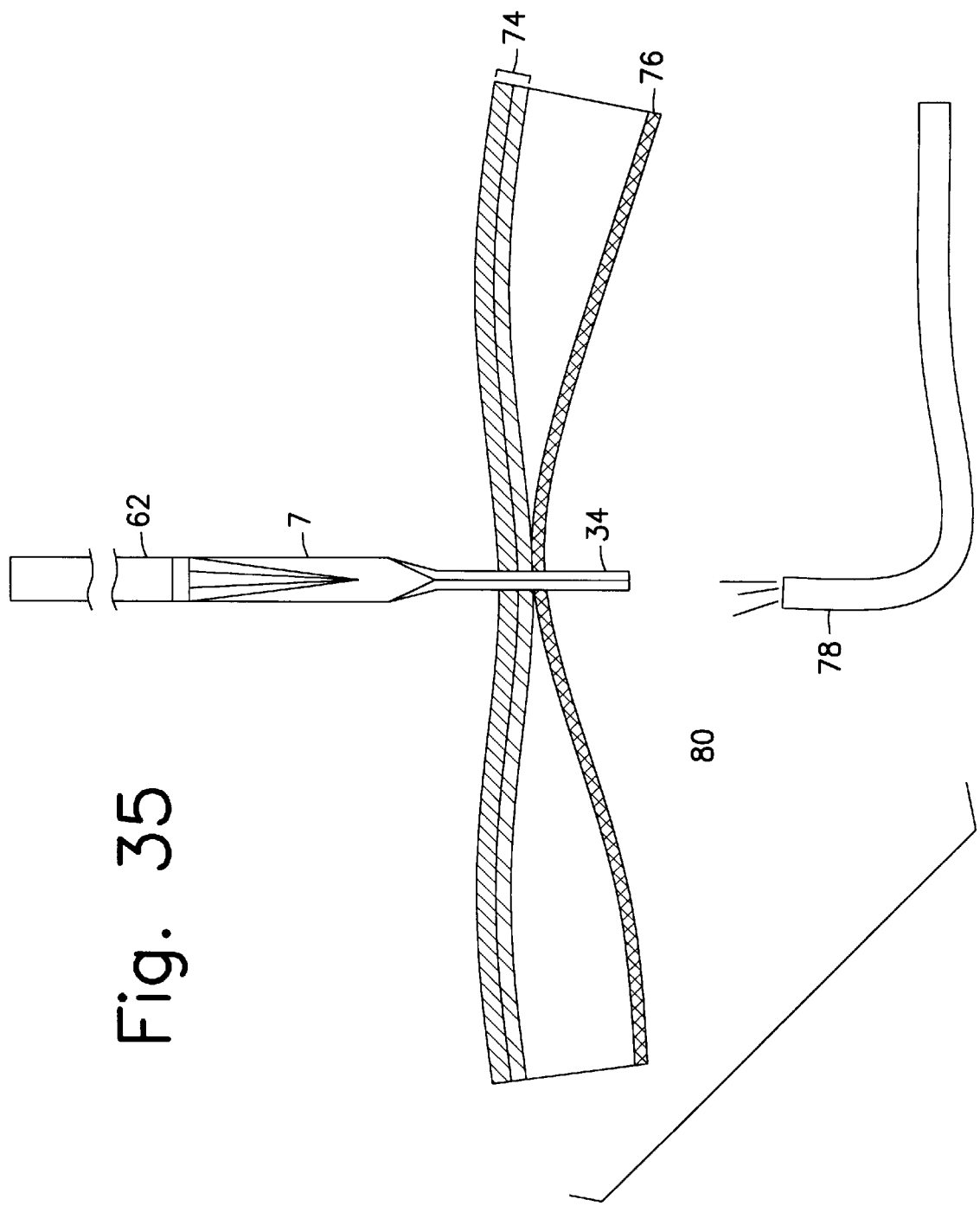
Figure 36:
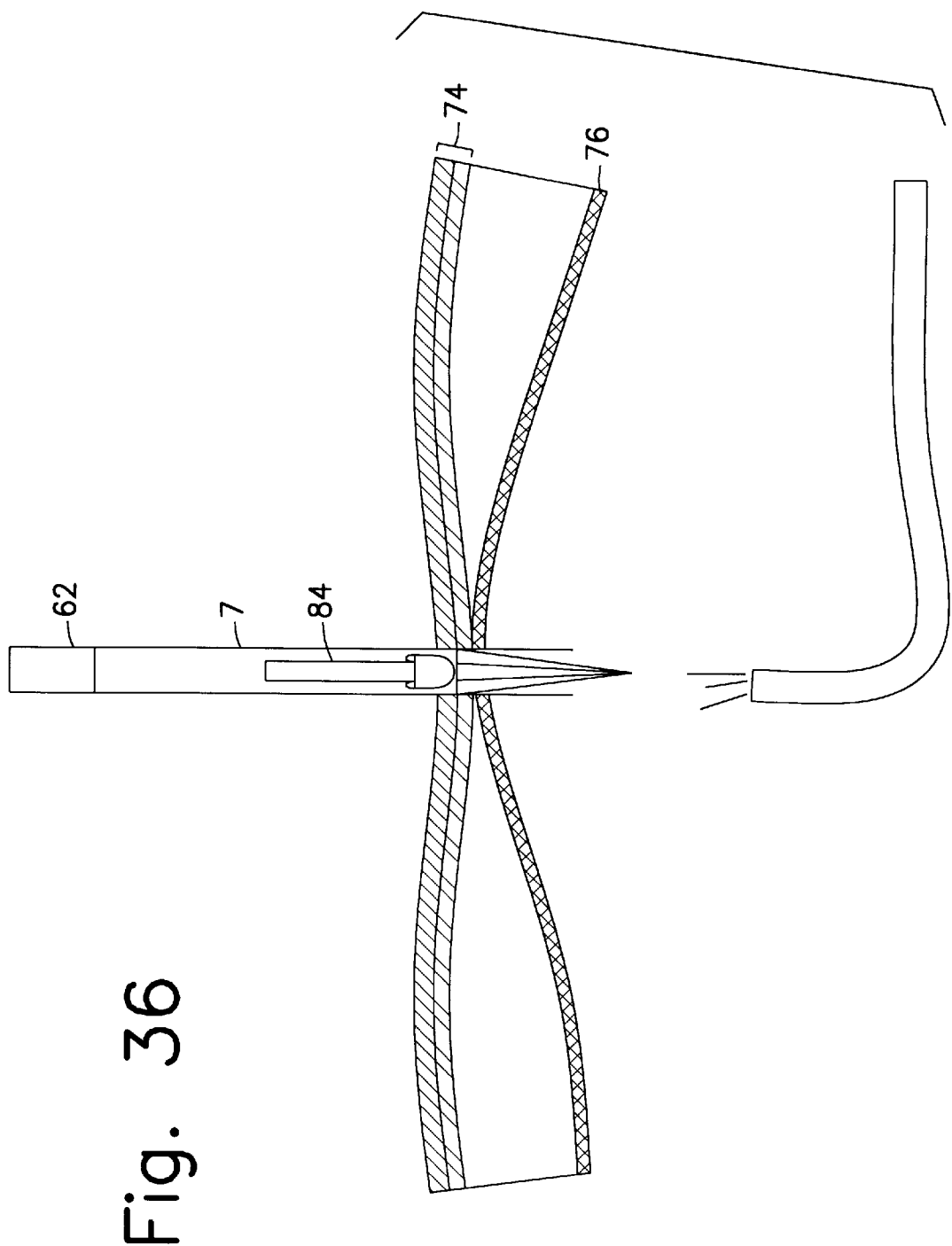

The apparatus of the current invention is then assembled such that the piercing means 60 of the penetration device 58 is located distally of the distal end of the radially expandable sheath 10. Under direct scope visualization, the assembly of the sheath 7 and penetration device 58 is then inserted through the abdominal wall 74, which consists of the patient's skin, a fat layer, fascia, and the peritoneum. The assembly is then further inserted into the gastric cavity 80. FIG. 33 shows the assembly as it is inserted into the organ cavity 80. The penetration device 58 is then removed, while the sheath 7 position within the penetration is maintained. FIG. 34 shows the sheath 7 in its maintained position with the penetration device 58 removed.

Figure 39:
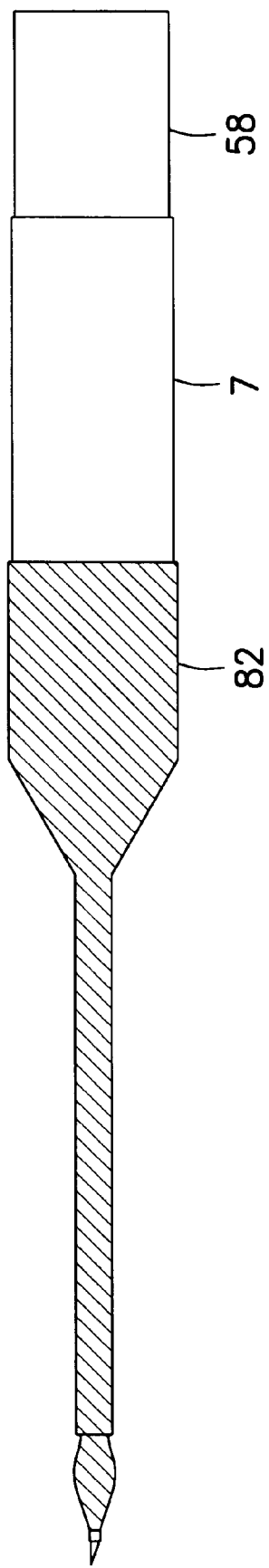
FIG. 39 is a sheath/penetration device assembly constructed according to the principles of the invention, in which the sheath covering extends over the penetration device.

Upon removal of the penetration device 58, some insufflation gas is likely to escape from the target organ. The sheath is constructed such that the degree to which insufflation gas can escape through the sheath material is limited. The sheath hub valve 52, described above, can also be used to prevent or limit escape of insufflation gas through the central lumen of the sheath 6.(See FIGS. 19–22). Alternatively, a covering or coating 82 may be placed over the sheath 7 such that this coating or covering 82 extends past the distal end of the sheath 7 to cover a portion of the penetration device's distal end 60, as shown in FIG. 39. The extending portion of the coating 82 has a very narrow opening at the distal end. The extending portion of the coating can be formed such that, once the penetration device 58 is removed, the extending portion of the coating can either remain in place or invert proximally into the sheath 7.

The narrow opening at the distal end of the coating limits the escape of insufflation gas from target organ.

Next, the hollow dilator 62 is placed within the radially expandable sheath 7, and pushed distally so as to force the sheath fingers 34 open, thereby enlarging the hole formed during the initial penetration. Simultaneously, the sheath 7 is pulled proximally so as to counter-balance the distal pressure, thus reducing the degree to which the anterior stomach wall 76 tents. As the dilator 62 is inserted using the counter-balancing method, the distal force applied to the body tissue at the point of insertion is converted into a force applied in the plane tangent to the organ wall, thereby reducing tenting of the target organ wall. In performing the dilator insertion of the present invention, the practitioner can push distally on the dilator 62 with one hand, while simultaneously counter-balancing the distal force by pulling on the radially expandable sheath 7 with the other hand. The sheath hub 50 and dilator hub 70 can act as handles to facilitate the counter-balancing.

The sheath coating or covering can be made of a material which expands or, alternatively, peels away as the dilator is inserted.

A gastrostomy tube 84 is preferably pre-loaded, i.e. placed within the dilator 62 prior to dilator insertion. Pre-loading alleviates the stress placed on the abdominal wall 74 and gastric 76 walls by reducing time necessary to perform percutaneous placement. Alternatively, the tube 84 may be placed within the dilator 62 during dilation, or after dilation is complete.

Figure 37:
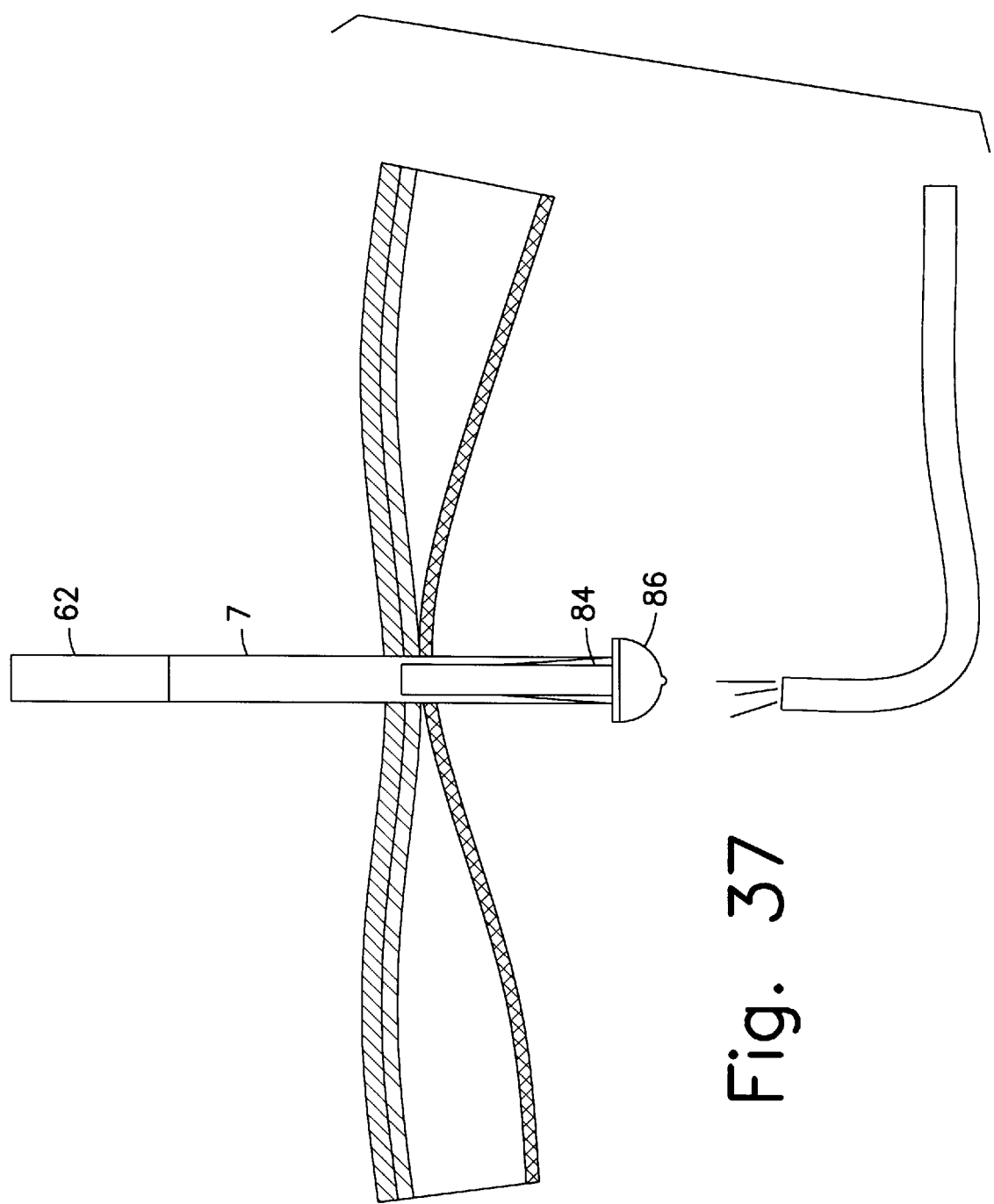
Figure 38:
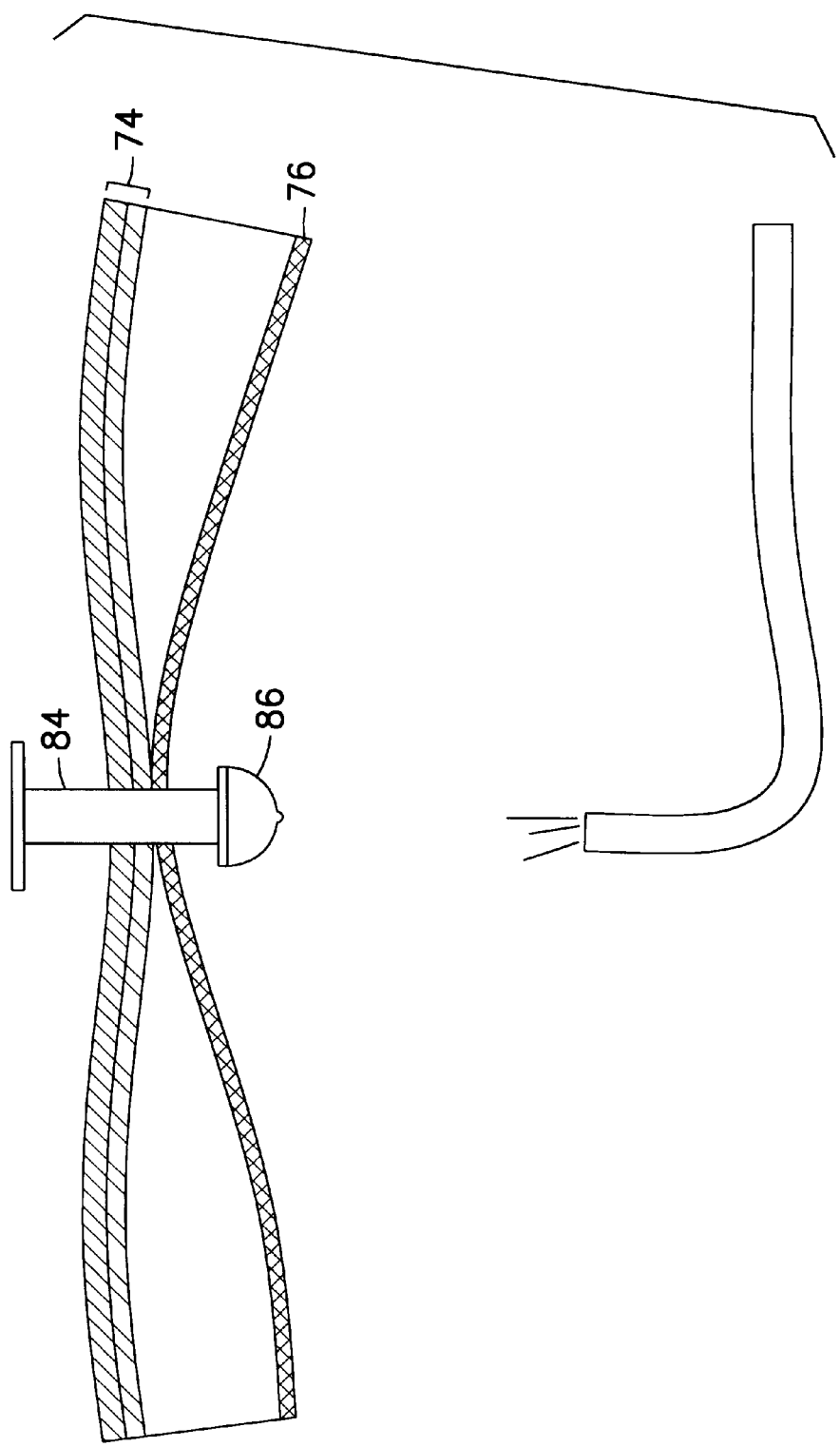

Once the dilator is in position and the gastrostomy tube 84 is placed within the central lumen of the dilator 62, an extension rod is placed into the proximal end of the dilator 62. The rod is pushed distally against the gastrostomy tube 84 while the sheath 7 and dilator 62 are held stationary. When the distal end of the tube 84 exits the dilator 62, as shown in FIG. 37, the extension rod position is maintained while the sheath 7 and dilator 62 are removed. The extension rod is then removed, leaving the distal end of the gastrostomy tube 84 in place within the stomach. From outside the abdomen, the tube 84 can then be adjusted, trimmed and secured with an external bolster 86.

The number of elements utilized to provide a force counter-force arrangement described above can be reduced through judicious choice of dilator geometry. For example, an additional embodiment of a dilator 98 is shown in FIGS. 40 and 41. Here, the dilator 98 has a "needle-nosed" appearance. In this embodiment the fingers 88 of the tapered distal end are formed by removing longitudinal sections from the tubular body such that when folded, as in FIG. 41, they form a straight section 92 and a proximally-adjacent graduated section 94. The straight section 92 has a minor diameter which is of a size capable of penetrating body tissue. The untapered tubular body 96 has a diameter which allows it to receive a gastrostomy tube. The diameter of the graduated section 94 decreases distally from that of the untapered tubular body 96 to the minor diameter of the straight section 92.

As with the previous embodiments, this needle-nosed dilator can be used in conjunction with the radially expandable sheath 10 and penetration device 58. It can also be used, by itself, to place a gastrostomy tube. A piercing means 90 may be detachably secured to the distal end of the hollow dilator 98 according to a fourth embodiment. The attached piercing 90 means eliminates the need for a separate penetration device. The dilator 98 equipped with the piercing means 90 is inserted into the body along with the radially expandable sheath 10. A gastrostomy tube is then forced through the dilator 62, causing the dilator 98 to expand and dislodge the piercing means 92.

The piercing means 92 can be made of a biocompatible polymer-based material which is left within the body to be passed through the alimentary canal. Alternatively, the piercing means 92 can be made of a biodegradable material and left within the body.

The dilator 98 according to the fourth embodiment can also be used without the radially expandable sheath 10. Instead, an elastomeric coating similar to that used with the sheath 10 can cover the straight 92 and graduated 94 sections. Using either the penetration device 58, or the attached piercing means 90, the needle-nosed dilator 98 is inserted into the body tissue 24 and 25 and through to the target site. The gastrostomy tube 30 is then forced through the dilator and placed within the desired organ.

Although this specification primarily discusses placement of gastrostomy tubes within the stomach, the apparatus and method of the present invention apply generally to placement of gastro-intestinal tubes in any number of places in the alimentary canal, including but not limited to the gastric cavity, jejunum, ileum, and colon. The category, "gastro-intestinal tubes," includes feeding tubes, access tubes, scope access ports, device access ports and the like.

Certain gastro-intestinal tubes have constant diameters throughout their length, such as operative ports for instrument or scope access. With these tubes, a solid dilator could be used instead of a hollow one. The tube would be placed over the dilator such that the tapered distal of the dilator extends distal of the distal tube end. The tube/dilator assembly would then be advanced through the sheath using the counter-balancing method described above. The dilator would then be removed from inside the tube, and the sheath removed from around the tube.

What is claimed is:

1. An apparatus for percutaneously placing a gastro-intestinal tube within a target organ comprising:
   a hollow dilator having a distal tapered section formed of longitudinal fingers, and an untapered tubular section proximal thereto, wherein the longitudinal fingers of the distal tapered section open radially in response to a force applied from inside the hollow center of the dilator;
   a sheath having proximal and distal ends, and a central lumen extending from the proximal end to the distal end, said sheath having a first inner diameter at the distal end, and a second inner diameter at the proximal end, wherein the second inner diameter is greater than the first inner diameter, and wherein said dilator is receivable within the central lumen of the sheath;
   a penetration device having proximal and distal ends, and a piercing means on the distal end, wherein said penetration device is receivable within the central lumen of the sheath.

2. An apparatus as in claim 1, wherein the longitudinal fingers of the dilator are formed such that the finger width decreases distally.

3. An apparatus as in claim 1, wherein the distal tapered section of the dilator is formed such that the longitudinal fingers are normally tapered to a point.

4. An apparatus as in claim 1, wherein the distal tapered section of the dilator is formed such that the longitudinal fingers of the dilator are normally untapered.

5. An apparatus as in claim 1, wherein the dilator is made of metal, thermoplastic, thermostat, or a composite.

6. An apparatus as in claim 1, wherein the dilator has a hub on the proximal end.

7. An apparatus as in claim 6, wherein the hub portion has a locking mechanism.

8. An apparatus as in claim 1, wherein the sheath is made of an expandable material.

9. An apparatus as in claim 1, wherein the outside surface of the sheath is treated to provide increased friction between the sheath and the abdominal tissue.

10. An apparatus as in claim 1, wherein the sheath has a thin, rigid coating which splits as the dilator passes through the central lumen of the sheath.

11. An apparatus as in claim 10, wherein the thin, rigid coating is longitudinally scored.

12. An apparatus as in claim 11, wherein the hub portion of the sheath has a locking mechanism.

13. An apparatus as in claim 11, wherein the hub portion has a valve for controlling the escape of insufflation gas.

14. An apparatus as in claim 13, wherein the valve consists of a thin, elastomeric disc having an opening capable of receiving the penetration device and dilator.

15. An apparatus as in claim 1, wherein the sheath has an elastomeric coating which expands as the dilator passes through the central lumen of the sheath.

16. An apparatus as in claim 15, wherein the elastomeric coating is longitudinally scored.

17. An apparatus as in claim 1, wherein the sheath has a coating which extends past the distal end of the sheath, whereby the coating forms a valve capable of limiting the amount of insufflation gas that can enter the distal end of the sheath.

18. An apparatus as in claim 1, wherein the sheath has a hub portion on the proximal end.

19. An apparatus as in claim 1, wherein the sheath has a diameter at its distal end which is less than or equal to 5 mm.

20. An apparatus as in claim 1, wherein sheath has a diameter at its proximal end which is greater than or equal to 7 mm. and less than or equal to 20 mm.

21. An apparatus as in claim 1, wherein the sheath has a distal minor diameter section and a major diameter section proximal thereto, with the minor diameter section comprising longitudinal fingers;
   wherein the longitudinal fingers of the distal minor diameter section of the sheath are capable of receiving the dilator as it passes through the central lumen of the sheath.

22. An apparatus as in claim 21, wherein the longitudinal fingers of the sheath are formed by slitting the sheath body longitudinally.

23. An apparatus as in claim 21, wherein the longitudinal fingers of the sheath are formed by removing longitudinal slices from the sheath body.

24. An apparatus as in claim 23, wherein the longitudinal slices are formed such that the finger width decreases distally.

25. An apparatus as in claim 21, wherein the minor diameter section of the sheath is formed by folding the longitudinal fingers.

26. An apparatus as in claim 21, wherein the minor diameter section of the sheath is formed by overlapping the longitudinal fingers.

27. An apparatus for percutaneously placing a gastro-intestinal tube within a target organ comprising:
   a hollow, needle-nosed dilator having proximal and distal ends, and a central lumen extending from the proximal end to the distal end, said dilator further having a distal tapered section formed of longitudinal fingers proximal and an untapered tubular section proximal thereto, whereby the distal tapered section consists of a distal straight section and a proximally-adjacent graduated section such that:

the straight section has a minor diameter; and the untapered tubular section has a major diameter which is greater than the minor diameter, and the graduated section has a diameter which decreases distally from the diameter of the untapered tubular body to the minor diameter of the straight section;

wherein the longitudinal fingers of the distal tapered section radially expand in response to a distal force from inside the hollow center of the dilator.

28. An apparatus as in claim 27, wherein the dilator has a piercing means detachably-secured to the distal end.

29. An apparatus as in claim 28, wherein the piercing means of the needle-nosed dilator is made of a biocompatible polymer-based material.

30. An apparatus as in claim 28, wherein the piercing means of the needle-nosed dilator is made of a biodegradable material.

31. An apparatus as in claim 27, wherein the distal tapered section is covered with an elastomeric coating.

32. An apparatus as in claim 31, wherein the elastomeric coating is longitudinally scored.

33. An apparatus as in claim 27, wherein the tapered section is covered with a thin, rigid coating.

34. An apparatus as in claim 33, wherein the thin, rigid coating is longitudinally scored.

35. A method for percutaneously placing a medical device within a target organ, said method comprising:

penetrating a target organ wall with an assembly of a sheath and a penetration device, the sheath having proximal and distal ends, and a central lumen extending from the proximal end to the distal end, and the penetration device having a piercing means at the distal end, and wherein the assembly is such that the penetration device is within the central lumen of said sheath such that the piercing means extends past the distal end of the sheath;

removing the penetration device from within the central lumen of the sheath in such a manner that the sheath remains within the target organ after removal of the penetration device;

inserting into the central lumen of the sheath a hollow dilator having a tapered distal end; and pushing said dilator distally through the central lumen of the sheath until it penetrates the target organ wall, while simultaneously pulling proximally on the sheath, whereby the diameter of the penetration in the target organ wall is increased.

36. The method as in claim 35, further comprising:

placing a gastro-intestinal tube having a proximal and a distal end into the hollow center of the dilator;

pushing the gastro-intestinal tube distally through the dilator until the distal end of the tube end exits the dilator;

removing the dilator from the target organ, while leaving the gastro-intestinal tube in place; and removing the sheath from the target organ.

37. A method for percutaneously placing a gastro-intestinal tube within a target organ, said method comprising:

insufflating a target organ;

penetrating a target organ wall with an assembly of an penetration device and a sheath in which the penetration device has a proximal end, a distal end, and a piercing means at its distal end, and the sheath has a proximal end, a distal end, and a central lumen extending from the proximal end to the distal end, the sheath further having a distal minor diameter section comprising longitudinal fingers formed such that the diameter at the distal end of the sheath is capable of penetrating body tissue, wherein the penetration device is within the central lumen of said sheath with the piercing means is distal of the distal end of the sheath;

removing said penetration device from said sheath in such a manner that the sheath remains within the target organ wall after removal of the penetration device;

inserting into the central lumen of the sheath a hollow dilator having a distal minor diameter section formed of longitudinal fingers and an untapered tubular section proximal thereto;

pushing said dilator through the central lumen of said sheath until the dilator penetrates the target organ wall, while simultaneously pulling proximally on the sheath to counter-balance the distal force, whereby the diameter of the penetration in the target organ wall is thereby increased;

placing a gastro-intestinal tube into the hollow center of said dilator;

pushing the gastro-intestinal tube distally through the dilator until the distal end of the tube exits the dilator, whereby the longitudinal fingers of the dilator are opened radially;

removing said sheath from the body tissue in such a manner that the gastro-intestinal tube remains within the target organ; and removing said dilator from the body tissue in such a manner that the gastro-intestinal tube remains within the target organ.

38. A method as in claim 37, wherein the dilator is pushed distally through the sheath with a distal force while the sheath is simultaneously pulled with a proximal force which is approximately the same as the distal force.

39. A method as in claim 37, wherein the dilator is pushed distally through the sheath with a distal force while the sheath is simultaneously pulled with a proximal force such that the planar position of the target organ wall remains substantially the same.

40. A method for percutaneously placing a medical device within a target organ, said method comprising:

penetrating the body tissue and target organ wall with a hollow needle-nosed dilator having a proximal end, a distal end, and a central lumen extending from the proximal end to the distal end, said dilator further having a straight section towards the distal end wherein the straight section is radially expandable and has a diameter capable of piercing the target organ, said straight section further having a piercing means detachably-secured to the distal end;

placing the medical device into the hollow center of said dilator;

pushing the medical device distally through the dilator until the distal end of the device exits the dilator, wherein the straight section of the dilator is radially expanded as the device passes through the central lumen of the dilator; and removing said dilator from the body tissue and target organ while maintaining the position of the medical device within the target organ.

41. A method for percutaneously placing a gastro-intestinal tube within a target organ, said method comprising:

insufflating a target organ;

penetrating the body tissue and target organ wall with a hollow thin-walled needle-nosed dilator having a proximal end, a distal end, and a central lumen extending from the proximal end to the distal end, said dilator further having a distal tapered section and an untapered tubular section proximal thereto, wherein the distal tapered section formed of longitudinal fingers and consists of a distal straight section and a proximally-adjacent graduated section, the the straight section having a diameter capable of penetrating body tissue, the untapered tubular section having a major diameter capable of receiving a gastro-intestinal tube, and the graduated section having a diameter which decreases distally from the diameter of the untapered tubular body to the minor diameter of the straight section;

placing a gastro-intestinal tube into the hollow center of said dilator;

pushing the gastro-intestinal tube distally through the dilator until the distal end of the tube exits the dilator, whereby the diameter of the penetration in the target organ wall is increased; and removing said dilator from the body tissue in such a manner that the gastro-intestinal tube remains within the target organ.

\* \* \* \* \*